(12) United States Patent
Oku et al.

(10) Patent No.: US 10,518,087 B2
(45) Date of Patent: Dec. 31, 2019

(54) DYSPHAGIA TEST DEVICE, DYSPHAGIA TEST METHOD, DYSPHAGIA TREATMENT DEVICE, AND STIMULATING CURRENT SETTING METHOD

(71) Applicants: HYOGO COLLEGE OF MEDICINE, Nishinomiya-shi, Hyogo (JP); CAREIDO Co., Ltd., Sagamihara-shi, Kanagawa (JP); J craft Co., Ltd., Izumi-shi, Osaka (JP); EuSense Medical Co., Ltd., Nishinomiya-shi, Hyogo (JP)

(72) Inventors: Yoshitaka Oku, Nishinomiya (JP); Hiroshi Ueno, Osakasayama (JP); Masahiro Waza, Nagoya (JP)

(73) Assignees: HYOGO COLLEGE OF MEDICINE, Hyogo (JP); J CRAFT CO., LTD., Osaka (JP); EUSENSE MEDICAL CO., LTD., Hyogo (JP)

( * ) Notice: Subject to any disclaimer, the term of this patent is extended or adjusted under 35 U.S.C. 154(b) by 23 days.

(21) Appl. No.: 15/854,195

(22) Filed: Dec. 26, 2017

(65) Prior Publication Data

US 2018/0117317 A1 May 3, 2018

Related U.S. Application Data

(63) Continuation of application No. PCT/JP2016/069396, filed on Jun. 30, 2016.

(30) Foreign Application Priority Data

Jun. 30, 2015 (JP) .................................. 2015-130747
Mar. 10, 2016 (JP) .................................. 2016-046616

(51) Int. Cl.
*A61N 1/36* (2006.01)
*A61B 5/00* (2006.01)

(52) U.S. Cl.
CPC .......... *A61N 1/3601* (2013.01); *A61B 5/4205* (2013.01); *A61B 5/4827* (2013.01); *A61N 1/36031* (2017.08); *A61N 1/36034* (2017.08)

(58) Field of Classification Search
CPC ................................ A61B 5/05; A61B 5/4205
See application file for complete search history.

(56) References Cited

U.S. PATENT DOCUMENTS

| 6,360,124 B1 | 3/2002 | Iwabuchi |
| 2013/0023952 A1 | 1/2013 | Freed |

(Continued)

FOREIGN PATENT DOCUMENTS

| CN | 104508343 A | 4/2015 |
| JP | H11-500339 A | 1/1999 |

(Continued)

OTHER PUBLICATIONS

Extended (supplementary) European Search Report dated Jul. 13, 2018, issued in counterpart European Application No. 16818009.9. (8 pages).

(Continued)

*Primary Examiner* — Alyssa M Alter
(74) *Attorney, Agent, or Firm* — Westerman, Hattori, Daniels & Adrian, LLP

(57) ABSTRACT

A dysphagia treatment device includes: a current application unit configured to be attached to a target portion of a treated person in order to percutaneously apply current to a biological tissue of the neck including superior laryngeal nerve of the treated person; a control unit configured to control the current application unit such that percutaneous stimulation caused by an interference wave or a pseudo interference wave is applied to the biological tissue of the neck including the superior laryngeal nerve; an operation unit configured to adjust the current to be applied by the current application (Continued)

unit, to a sensory threshold at which the treated person becomes aware of the percutaneous stimulation; and a display unit configured to display index information based on the sensory threshold.

13 Claims, 15 Drawing Sheets

(56) References Cited

U.S. PATENT DOCUMENTS

| 2014/0236262 | A1* | 8/2014 | You | A61B 8/08 607/59 |
|---|---|---|---|---|
| 2015/0165201 | A1 | 6/2015 | Oku | |
| 2016/0143575 | A1 | 5/2016 | Oku et al. | |

FOREIGN PATENT DOCUMENTS

| JP | 2001-029485 A | 2/2001 |
|---|---|---|
| JP | 2007-151736 A | 6/2007 |
| JP | 2007-151747 A | 6/2007 |
| JP | 2011-4968 A | 1/2011 |
| JP | 2014-529413 A | 11/2014 |
| JP | 2015-62487 A | 4/2015 |
| KR | 2001-0014493 A | 2/2001 |
| KR | 10-1006109 B1 | 1/2011 |
| KR | 2012-0099941 A | 9/2012 |
| KR | 10-2015-0032757 A | 3/2015 |
| WO | 97/15349 A1 | 5/1997 |
| WO | 2013/113023 A1 | 8/2013 |
| WO | 2015/029501 A1 | 3/2015 |

OTHER PUBLICATIONS

Office Action dated Aug. 3, 2018, issued in counterpart Chinese Application No. 201680039201.X, with English translation. (17 pages).

Notification of Reason for Refusal dated Apr. 17, 2018, issued in counterpart Japanese application No. 2017-526424, with English translation. (7 pages).

Office Action dated May 1, 2018, issued in counterpart Korean application No. 10-2018-7002363, with Japanese and English translation. (26 pages).

International Search Report dated Sep. 6, 2016, issued in counterpart application No. PCT/JP2016/069396, w/ English translation. (4 pages).

"Proposal of New Electric Stimulation Device for Rehabilitation 'Gentle Stim'", Jcraft, Sep. 11, 2015, w/English partial translation (4 pages).

Written Opinion dated Sep. 6, 2016, issued in counterpart application No. PCT/JP2016/069396, w/English translation, (7 pages).

* cited by examiner

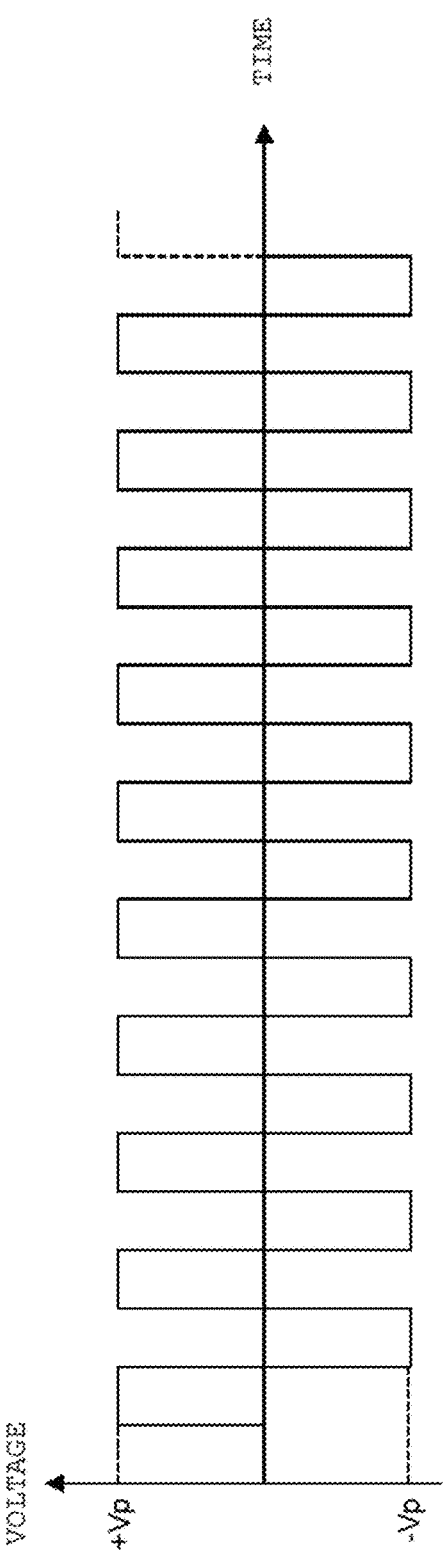
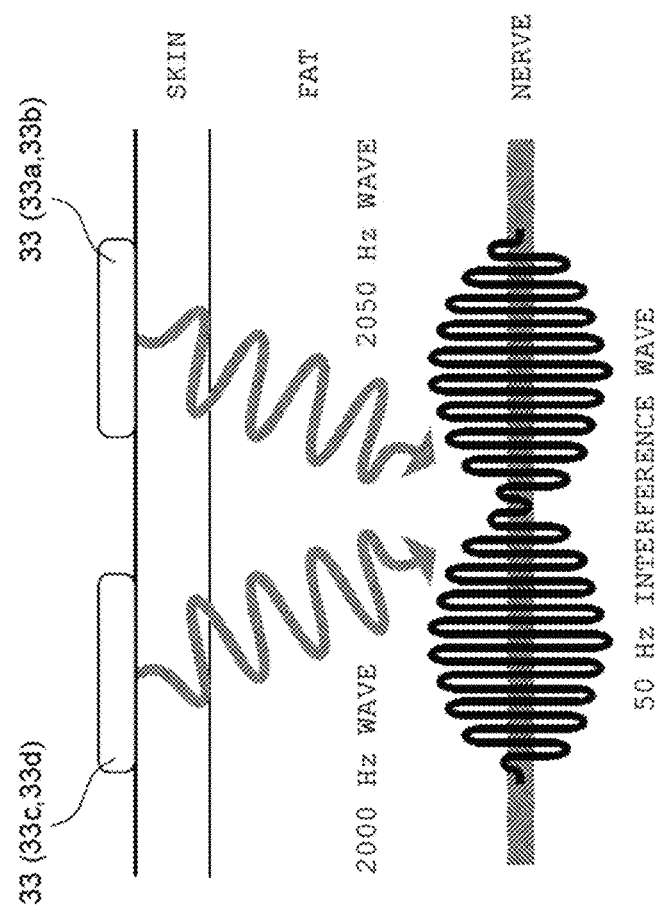
Fig. 8A
Fig. 8B

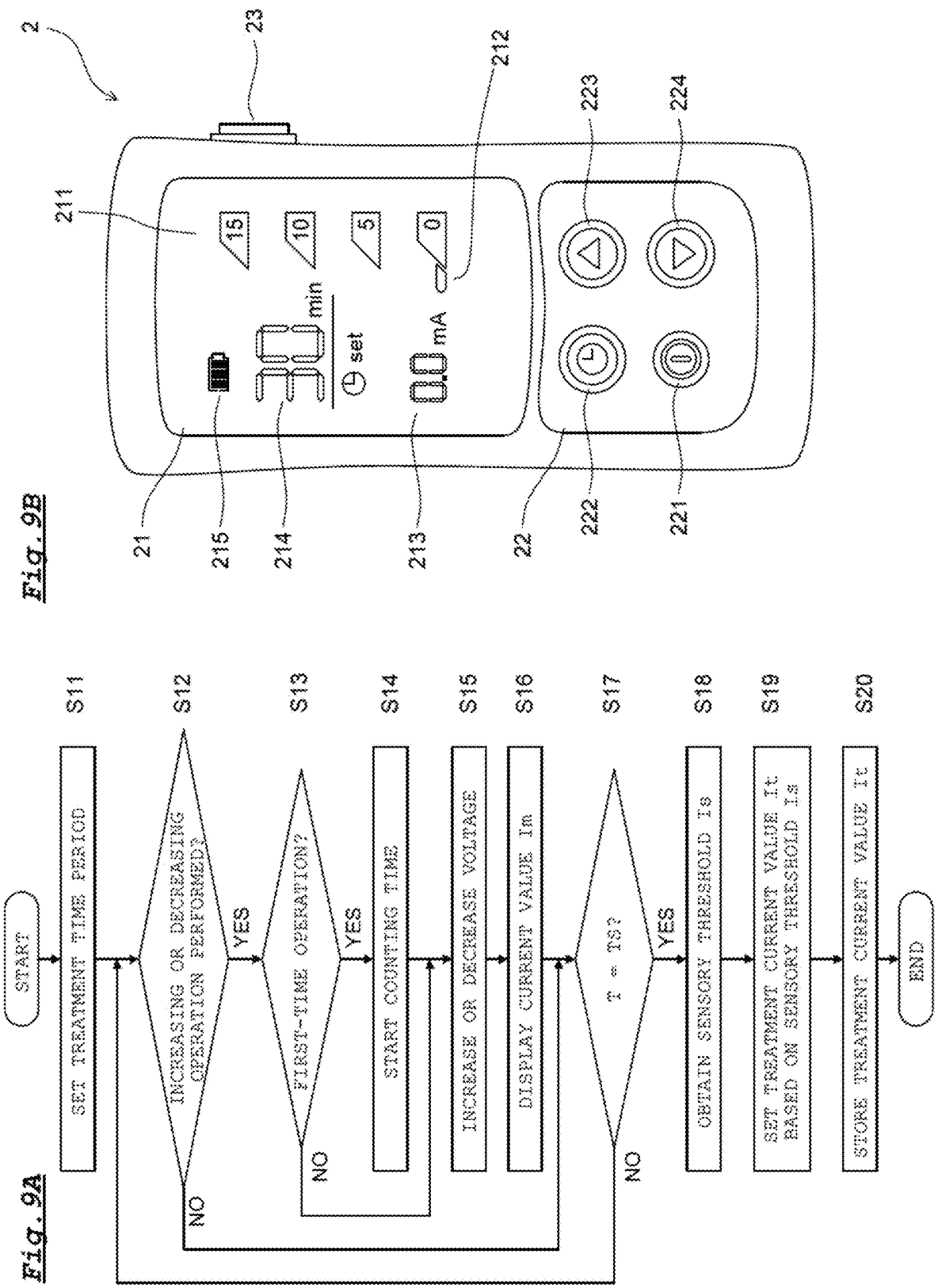

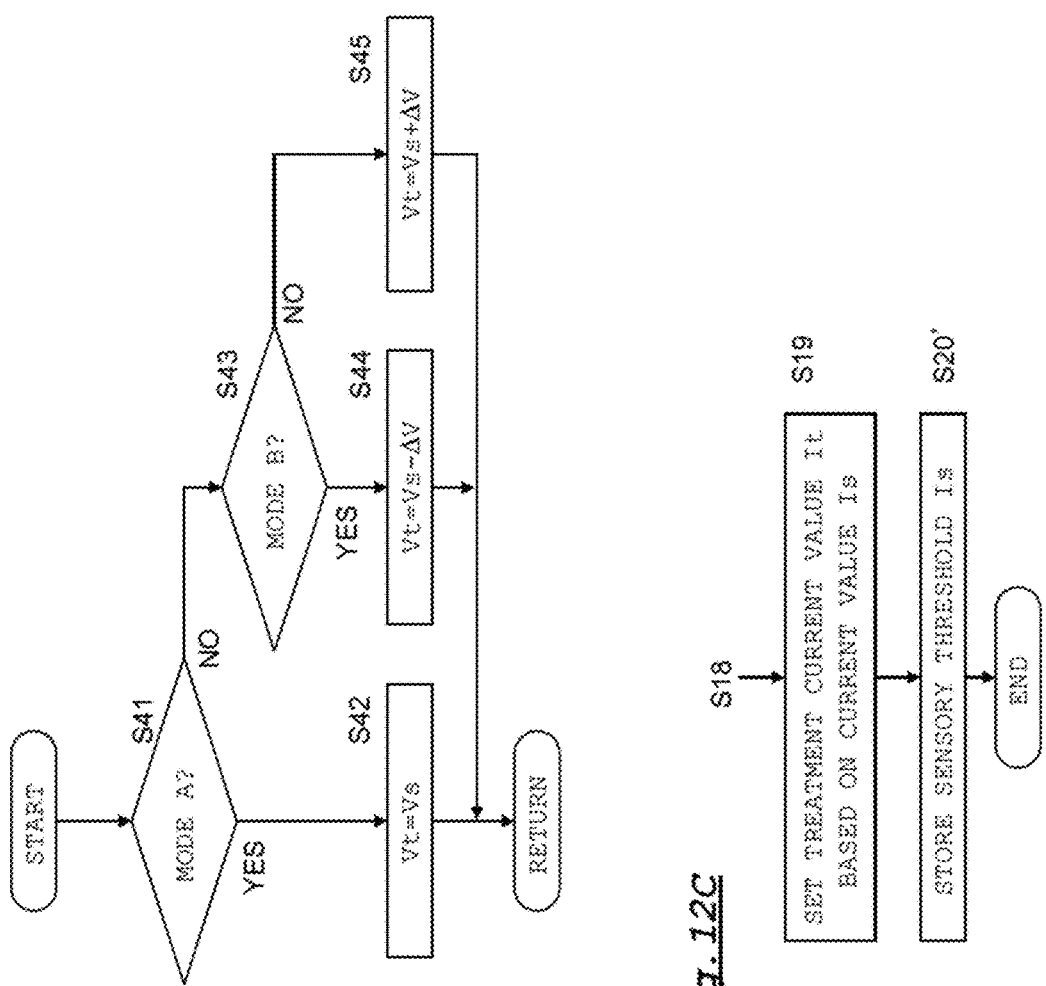
Fig.12B
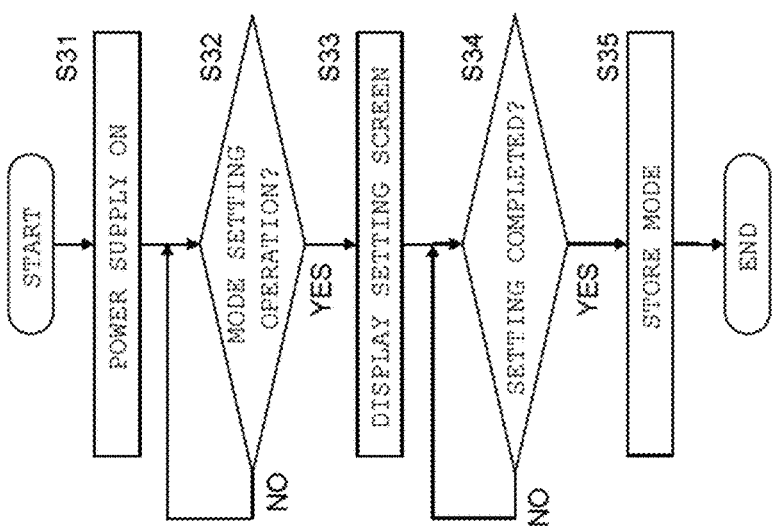
Fig.12C
Fig.12A

DYSPHAGIA TEST DEVICE, DYSPHAGIA TEST METHOD, DYSPHAGIA TREATMENT DEVICE, AND STIMULATING CURRENT SETTING METHOD

CROSS REFERENCE TO RELATED APPLICATION

This application is a continuation of International Application No. PCT/JP2016/069396 filed on Jun. 30, 2016, entitled "DYSPHAGIA TEST DEVICE, DYSPHAGIA TEST METHOD, DYSPHAGIA TREATMENT DEVICE, AND STIMULATING CURRENT SETTING METHOD", which claims priority under 35 U.S.C. Section 119 of Japanese Patent Application No. 2015-130747 filed on Jun. 30, 2015, entitled "DYSPHAGIA TEST METHOD" and Japanese Patent Application No. 2016-046616 filed on Mar. 10, 2016, entitled "DYSPHAGIA TEST DEVICE, DYSPHAGIA TEST METHOD, DYSPHAGIA TREATMENT DEVICE, AND STIMULATING CURRENT SETTING METHOD". The disclosure of the above applications is incorporated herein by reference.

BACKGROUND OF THE INVENTION

1. Field of the Invention

The present invention relates to a dysphagia test device and a dysphagia test method which are suitable for use in dysphagia tests, and relates to a dysphagia treatment device and a stimulating current setting method suitable for use in treatment of dysphagia.

2. Disclosure of Related Art

Swallowing is an action of taking something in and sending it to the stomach, and is performed through a series of complicated motions of the oral cavity, the pharynx, and the esophagus. Dysphagia means that there is disorder somewhere in the series of motions. Dysphagia includes aspiration in which the thing that has been taken through the mouth enters the trachea, not the esophagus.

Dysphagia could be caused by various diseases. Examples of such diseases that cause dysphagia include stroke aftereffect, traumatic brain injury, cerebral palsy, dementia, Parkinson's disease, Huntington's disease, Wilson's disease, amyotrophic lateral sclerosis (ALS), multiple sclerosis, brain tumor, and myasthenia gravis.

As a therapy for dysphagia, the inventors of the present application previously provided a technique of percutaneously stimulating the superior laryngeal nerve by use of an interference wave (PATENT LITERATURE 1: Japanese Laid-Open Patent Publication No. 2007-151736). In this technique, two or more pairs of electrodes, each pair consisting of a positive-side electrode and a negative-side electrode, are prepared. A control unit causes current having a predetermined frequency (carrier frequency) to flow from these electrodes to be percutaneously applied to the pharynx portion. At this time, the difference in frequencies among the electrodes (treatment frequency) is adjusted to 10 to 100 Hz. Further, from the electrodes of each pair, output is performed for 1 to 1000 ms and output is stopped for 1 to 1000 ms. These operations are alternately repeated in a continuous manner.

Furthermore, the inventors of the present application provided various techniques of monitoring the swallowing activity, other than the therapy (PATENT LITERATURE 2: Japanese National Phase PCT Laid-Open Publication No. 2009-151324, PATENT LITERATURE 3: WO15/029501).

For example, in the swallowing activity monitoring device described in PATENT LITERATURE 2, suprasternal fossa portion pressure information according to a motion of the suprasternal fossa portion of a subject is read out from a storage medium, and further, respiration flow information according to the respiration activity of the subject is read out from the storage medium. Then, on the basis of the read suprasternal fossa portion pressure information and respiration flow information, the swallowing activity of the subject is detected.

Meanwhile, a swallowing estimation device described in PATENT LITERATURE 3 includes: a sound sensor which detects sound of the larynx portion; a pressure sensor which detects respiration; and a control unit which estimates swallowing on the basis of biological sound data based on a sound signal outputted from the sound sensor and on the basis of airflow pressure data based on a pressure signal outputted from the pressure sensor. Then, the control unit obtains a value of parameter for swallowing estimation with respect to a biological sound generation interval that corresponds to an apneic interval longer than or equal to 400 msec, and estimates whether swallowing has occurred in the biological sound generation interval on the basis of whether the obtained value of the parameter satisfies a swallowing determination condition.

In diagnosis and treatment of swallowing, it is preferable that the presence or absence or the degree of disorder of dysphagia, and the degree of improvement of dysphagia attained by treatment of swallowing can be determined in a simple and appropriate manner, and it is preferable that treatment of dysphagia can be effectively carried out.

SUMMARY OF THE INVENTION

One aspect of the present invention lies in that dysphagia of a treated person is evaluated by using, as an evaluation index, a sensory threshold obtained by use of percutaneous stimulation caused by an interference wave or a pseudo interference wave. Here, the sensory threshold means a threshold of current which allows, when a weak current is percutaneously applied to a biological tissue of the neck including superior laryngeal nerve in order to apply percutaneous stimulation caused by an interference wave or a pseudo interference wave, a treated person to subjectively sense stimulation caused by the weak current.

In this aspect, the evaluation of dysphagia can be performed in terms of at least one of the presence or absence of dysphagia, the degree of dysphagia, and the degree of improvement attained by treatment of dysphagia.

In order to obtain the sensory threshold, a configuration can be employed in which one pair or two or more pairs of electrodes, each pair consisting of a positive-side electrode and a negative-side electrode, are set at the neck, the frequency of current applied by these electrodes is set to 500 to 8000 Hz, and the difference between the frequencies among the electrodes is set to 10 to 100 Hz, whereby stimulation caused by an interference wave or a pseudo interference wave is applied to the treated person.

In this case, preferably, the paired electrodes are able to be adhered, in parallel or in an X-like shape, to the neck, and are thin and flexible electrodes.

Stimulation may be provided at an output of 0 to 10 mA (effective value attained when a 500Ω load resistor is connected), and the value that has allowed the treated person to become aware of stimulated feeling due to stimulation may be specified as the sensory threshold.

In this case, the specified sensory threshold is recorded and saved in a time-based manner, and the saved data may be called when necessary, and the called data may be compared with initial data, history data, progressive average data, or known dysphagia data.

A dysphagia test device according to this aspect includes: a current application unit configured to be attached to a target portion of a treated person in order to percutaneously apply current to a biological tissue of a neck including superior laryngeal nerve of the treated person; a control unit configured to control the current application unit such that percutaneous stimulation caused by an interference wave or a pseudo interference wave is applied to the biological tissue; an operation unit configured to adjust the current to be applied by the current application unit, to a sensory threshold at which the treated person becomes aware of the percutaneous stimulation; and a display unit configured to display index information based on the sensory threshold.

A dysphagia test method according to this aspect includes the steps of: applying percutaneous stimulation caused by an interference wave or a pseudo interference wave to a biological tissue of a neck including superior laryngeal nerve of a treated person, by percutaneously applying current from electrodes attached to the neck of the treated person; obtaining a threshold of the current at which the treated person senses the stimulation; and displaying information based on the obtained threshold of the current, as an evaluation index for dysphagia.

According to the dysphagia test device and the dysphagia test method configured as above, index information based on the sensory threshold at which the treated person becomes aware of percutaneous stimulation is displayed as an evaluation index for dysphagia. Thus, with the outputted index information, the operator can evaluate the state of dysphagia of the treated person.

Another aspect of the present invention lies in that, in treatment of dysphagia, the sensory threshold obtained by the above-described method is used for setting the percutaneous stimulation caused by an interference wave or a pseudo interference wave. In this aspect, when percutaneous stimulation caused by an interference wave or a pseudo interference wave is consecutively or intermittently applied in the treatment to a biological tissue of the neck including the superior laryngeal nerve, the sensory threshold obtained by the above-described method is used as an index for setting an individual optimum stimulation condition which is an optimum stimulation condition for each treated person.

In this aspect, percutaneous stimulation caused by an interference wave or a pseudo interference wave for treatment of dysphagia can be provided in the following manner: for example, one pair or two or more pairs of electrodes, each pair consisting of a positive-side electrode and a negative-side electrode, are set at the neck, the frequency of current applied by these electrodes is set to 500 to 8000 Hz, the difference in the frequencies among the electrodes is set to 10 to 100 Hz, and further, current is outputted from these electrodes consecutively or intermittently for 10 minutes to 8 hours.

In this case, intermittent provision of interference can be performed by consecutively performing, for 10 minutes to hours, repetition of a process of applying an interference wave for 0.05 to 5 seconds and a process of applying a non-interference wave for 0.05 to 5 seconds, for example.

The condition of intermittently outputting current by the electrodes may be set such that outputting current for 0.05 to 5 seconds and stopping for 0.05 to 5 seconds of output of current are alternately repeated in a continuous manner.

A dysphagia treatment device according to this aspect includes: a current application unit configured to be attached to a target portion of a treated person in order to percutaneously apply current to a biological tissue of a neck including superior laryngeal nerve of the treated person; a control unit configured to control the current application unit such that percutaneous stimulation caused by an interference wave or a pseudo interference wave is applied to the biological tissue; and an operation unit configured to adjust the current to be applied by the current application unit, to a sensory threshold at which the treated person becomes aware of the percutaneous stimulation. Here, the control unit sets, for the current application unit, a current value for treatment to be provided to the treated person, on the basis of the sensory threshold adjusted through the operation unit.

A stimulating current setting method according to this aspect includes the steps of: applying percutaneous stimulation caused by an interference wave or a pseudo interference wave to a biological tissue of a neck including superior laryngeal nerve of a treated person, by percutaneously applying current from electrodes attached to the neck of the treated person; obtaining a threshold of the current at which the treated person senses the stimulation; and setting a current value for treatment on the basis of the obtained threshold of the current, and causing the current to be outputted from the electrodes at the set current value.

According to the dysphagia treatment device and the stimulating current setting method configured as above, the current value for treatment is adjusted in accordance with the level of dysphagia of the treated person. Thus, stimulation appropriate for the level of dysphagia of the treated person can be percutaneously applied to a biological tissue of the neck including the superior laryngeal nerve of the treated person, and treatment of dysphagia can be effectively carried out.

In each aspect of the present invention, "percutaneously applying current to a biological tissue of the neck including superior laryngeal nerve" has a broad meaning that includes percutaneous application of current to the superior laryngeal nerve at the neck, and percutaneous application of current to a range including: the superior laryngeal nerve at the neck; nerves therearound, such as glossopharyngeal nerve and trigeminal nerve; muscles; and the like.

BRIEF DESCRIPTION OF THE DRAWINGS

FIG. 8A is a schematic diagram showing the waveform of voltage applied from the electrodes, according to the embodiment;

FIG. 8B is a schematic diagram showing the action by the dysphagia treatment device, according to the embodiment;

FIG. 9A is a flow chart showing a process for setting a treatment current value, according to the embodiment;

FIG. 9B is a diagram showing a configuration of a screen to be displayed on a display unit of the treatment unit body and a configuration of an operation unit thereof, according to the embodiment;

FIG. 12A is a flow chart showing a mode setting process according to Modification 1;

FIG. 12B is a flow chart showing a process for setting the treatment current value according to Modification 1;

FIG. 12C is a flow chart showing a process for setting the treatment current value according to Modification 2;

Figure 1:
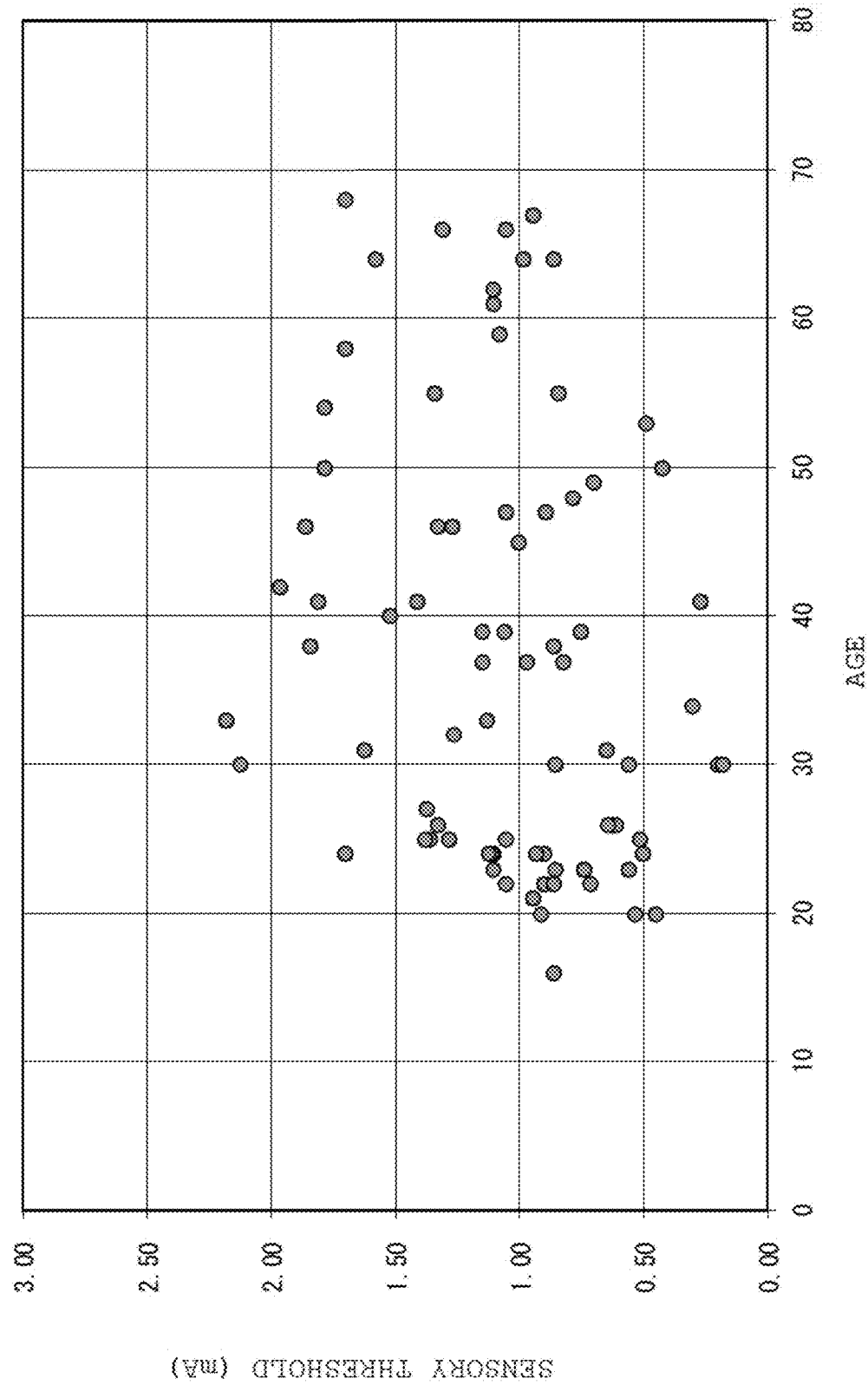
FIG. 1 is a graph showing a measurement result of distribution of sensory thresholds of healthy individuals according to an embodiment.

It should be noted that the drawings are solely for description and do not limit the scope of the present invention by any degree.

DESCRIPTION OF THE PREFERRED EMBODIMENTS

1. Dysphagia Test Method

One mode of the present invention can be considered as a method for testing dysphagia by using, as a marker for dysphagia evaluation, a sensory threshold obtained by percutaneously applying stimulation of an interference wave or a pseudo interference wave.

Here, the sensory threshold to be used as a marker for dysphagia evaluation means the smallest value of current that allows, when weak current is percutaneously applied to the neck for several seconds, a treated person (patient) to subjectively sense stimulation caused by the weak current, i.e., a threshold of current sensed by somatosensory nerves. For example, measurement of the sensory threshold is performed as follows.

First, an operator such as a doctor attaches electrodes to the neck of a patient, then, causes a stimulation device (or a dysphagia treatment device itself) to operate, the device for applying stimulation caused by an interference wave or a pseudo interference wave by means of the electrodes, and causes the electrodes to output weak current. Next, the operator gradually increases the output of the weak current, has the patient make notification at the time point when the patient has become aware of stimulation caused by the weak current, and measures the current value at that time point as a sensory threshold. The measurement of the current value is performed with an ammeter set to an electrode cable of the stimulation device, for example. Alternatively, a system may be used in which, in response to an input performed by the patient indicating that the patient has become aware of stimulation, the current value at that timing is displayed.

In a case where the stimulation device is equipped with a current value measurement function, the operator attaches electrodes to the neck of a patient, then, causes the stimulation device (dysphagia treatment device) to operate, and gradually increases the output, in a manner similar to that described above. The operator has the patient make notification at the time point when the patient has become aware of stimulation caused by the weak current, and performs, on the stimulation device, an input for fixing and/or recording the output level of the current at that time point. Accordingly, the stimulation device measures the current value at that time point by a current detection and display function built in the device in advance, and sets the measured current value as a sensory threshold. That is, by the operator performing an input for fixing the level of the current output at the time point when the patient has become aware of weak current, the current value is automatically recorded and saved as data in the stimulation device. The operator calls the current value saved as data, to confirm the measurement value. This measurement value is the sensory threshold. It should be noted that the input for fixing a current value may be performed by a patient, not by an operator.

For example, in a case where stimulation caused by an interference wave is applied in order to obtain a sensory threshold, two pairs of electrodes, each pair consisting of a positive-side electrode and a negative-side electrode, are set at the neck. Meanwhile, in a case where stimulation caused by a pseudo interference wave is applied in order to obtain a sensory threshold, one pair of electrodes, the pair consisting of a positive-side electrode and a negative-side electrode, are set at the neck. The frequency of current applied from these electrodes is set to 500 to 8000 Hz, the difference in frequencies between these electrodes is set to 10 to 100 Hz, and treatment on the treated person is performed. The stimulation targets a biological tissue of the neck including the superior laryngeal nerve, i.e., the superior laryngeal nerve and nerves and muscles around the superior laryngeal nerve (hereinafter referred to as "the superior laryngeal nerve, etc."). Preferably, with respect to the electrodes, the paired electrodes are adhered, in parallel or in an X-like shape, to the neck. In addition, thin and flexible electrodes are preferably used.

Stimulation caused by an interference wave or a pseudo interference wave and percutaneously applied is provided at an output of 0 to 10 mA (effective value attained when a 500Ω load resistor is connected). A value, of this output, that has allowed the treated person to become aware of stimulated feeling is specified as the sensory threshold. The output is increased automatically or non-automatically, in an inclined manner or stepwise. The sensory threshold of the treated person is saved as data by means for specifying and fixing the sensory threshold. The value of the sensory threshold is expressed in a unit of mA (milliampere), for example.

Actual measurement performed by the inventors of the present application revealed that the average of the sensory thresholds obtained from 81 healthy adults was 1.05 mA (also referred to as progressive average data, for example). Meanwhile, measurement was performed on patients specified as persons with dysphagia through determination using laryngeal elevation delay time (LEDT) (also referred to as known dysphagia data, for example) which is a known dysphagia degree evaluation, and these patients exhibited sensory thresholds of 2.5 mA or greater. In Example described later, in interference wave stimulation treatment for persons with dysphagia, both of sensory threshold and LEDT were measured, and the correlation therebetween was confirmed. As a result, correlation between the numerical value of the sensory threshold and the degree of dysphagia was confirmed. Thus, the inventors of the present application succeeded in providing a dysphagia test method in which the sensory threshold is used as a marker for dysphagia test.

The presence or absence of dysphagia can be determined on the basis of a numerical value up to 2.5 mA in consideration of individual difference, using an average sensory threshold (around 1.05 mA, for example) of healthy adults as a reference. In this case, the higher the sensory threshold is, the higher the possibility of dysphagia is. In level determination of the degree of disorder of dysphagia, the higher the sensory threshold is, the higher the degree of disorder of dysphagia could be. In level determination of the degree of improvement attained by treatment of dysphagia, the lower than the initial sensory threshold the sensory threshold measured during treatment is, the higher the degree of improvement attained by treatment of dysphagia could be.

A method for realizing measurement of the sensory threshold by the stimulation device (or the dysphagia treatment device, the same applies hereinafter) using an interference wave or a pseudo interference wave is as follows.

The stimulation device is equipped with a circuit for measuring current during treatment, can measure the current value of the sensory threshold by use of a built-in ammeter, and can display an output level on a display unit of the device body. In addition, the device is equipped with an element or a medium for recording and saving data; can record and save, as data of the sensory threshold, the measured current value of the sensory threshold into the device body; can call, through an operation performed onto the device, the current value of the sensory threshold saved as data; and can display the called current value on the display unit of the body.

Further, the device can record and save a plurality of measured current values, as data. The device can record, save, and output the measured current values of the sensory threshold, as history data. The operator such as a doctor can sequentially call also the history data of the recorded current values of the sensory threshold, through an operation performed onto the device. Thus, the operator can call and confirm a past current value of the sensory threshold, and can determine whether the patient has dysphagia through comparison with a reference value (about 2.5 mA when data of Example described later is used as a reference, for example) of the sensory threshold regarding dysphagia. Further, the operator can confirm the degree of improvement attained by the treatment of dysphagia, by confirming a plurality of past current values of the sensory threshold recorded in the device.

2. Method for Setting Stimulation Condition for Treatment of Dysphagia

Another mode of the present invention can be considered as a method for setting an optimum stimulation condition for each patient (individual optimum interference wave stimulation condition) in the dysphagia treatment device on the basis of the obtained sensory threshold, and can be considered as a treatment method for causing the dysphagia treatment device to operate on the basis of the set optimum condition. Here, for treatment of dysphagia, the superior laryngeal nerve, etc. are percutaneously stimulated by an interference wave or a pseudo interference wave. Electric output is performed consecutively or intermittently, whereby the interference is consecutively or intermittently caused. Operation of the dysphagia treatment device can be executed in a manner linked with or not linked with the settings of the optimum condition.

The individual optimum interference wave stimulation condition is set, using the sensory threshold as a marker. The sensory threshold is consecutively recorded and saved as history data, from the start of treatment in dysphagia therapy for the individual (patient) and in accordance with the progress of the therapy.

When the initial data of the sensory threshold is specified, an initial optimum interference wave stimulation condition (carrier frequency, treatment frequency, process output, output mode, output time, etc.) set in advance is selected in accordance with the initial sensory threshold and the age, sex, and the like of the patient, and an initial individual optimum interference wave stimulation condition is set. Through this setting, an operation condition of the dysphagia treatment device corresponding to each value of the set condition is specified in a linked manner or in a non-linked manner, and under the specified operation condition, operation of the dysphagia treatment device is executed.

When the sensory threshold has varied as a result of treatment, an optimum interference wave stimulation condition (carrier frequency, treatment frequency, process output, output mode, output time, etc.) set in advance is selected in accordance with the basic information (initial sensory threshold, age, sex, etc.) and the varied sensory threshold, and an individual optimum interference wave stimulation condition is set. Through this setting, an operation condition of the dysphagia treatment device corresponding to each value of the set condition is specified in a linked manner or in a non-linked manner, and accordingly, the operation condition of the dysphagia treatment device is changed to a condition according to the variation of the sensory threshold. Under the changed operation condition, operation of the dysphagia treatment device is executed.

The individual optimum interference wave stimulation condition is selected by use of means capable of selecting a level of stimulation caused by an interference wave for treatment of dysphagia. The condition of stimulation caused by an interference wave or a pseudo interference wave is selected and specified by use of means that can, with one pair or two or more pairs of electrodes set at the neck, each pair consisting of a positive-side electrode and a negative-side electrode, set the frequencies of currents applied by these electrodes to 500 to 8000 Hz; that can set the difference in the frequencies among the electrodes to 10 to 100 Hz; and further, that can cause output from these electrodes to be performed consecutively or intermittently for 10 minutes to 8 hours.

Stimulation by an interference wave causes less skin pain or discomfort, and allows a low frequency wave to reach the depth under the skin. For example, when percutaneous electric stimulation is caused at medium frequency waves of 2000 Hz and 2050 Hz, a low frequency wave of 50 Hz is generated at the depth under the skin. The medium frequency used in the stimulation at this time is referred to as carrier frequency, and the generated low frequency is referred to as beat frequency (treatment frequency).

It is desired that the carrier frequency is 500 to 8000 Hz, preferably 1000 to 4000 Hz, and further preferably 1500 to 3000 Hz. The reason for this is as follows: in the case of a current having a frequency lower than 500 Hz, subcutaneous nociceptors respond more strongly and transmit pain sensation to the central nervous system, and in the case of a current having a frequency higher than 8000 Hz, muscle contraction can no longer follow each stimulation pulse and muscles are in a contacted state in the entire period in which the current is being applied.

The beat frequency, i.e., the dysphagia treatment frequency, is selected from 10 to 100 Hz, preferably 20 to 80 Hz, further preferably 30 to 60 Hz. The reason why the range of the treatment frequency is set to 10 to 100 Hz is that it is determined that this frequency band can cause strongest response of receptors relevant to dysphagia cure and is the most effective band for stimulation of the superior laryngeal nerve.

Regarding stimulation caused by an interference wave for treatment of dysphagia, as one method for processing an interference wave, there is a method in which interference is intermittently caused. This method is a method in which repetition of a process of outputting an interference wave for 0.05 to 5 seconds and a process of outputting a non-interference wave for 0.05 to 5 seconds is performed consecutively for 10 minutes to 8 hours. Another preferable processing method is a method in which only an interference wave or a pseudo interference wave is intermittently outputted. This method is a method in which a process of outputting an interference wave for 0.05 to 5 seconds and a process in which output of the interference wave is stopped for 0.05 to 5 seconds are alternately repeated in a continuous manner. Another preferable processing method is a method in which an interference wave is continuously outputted, consecutively for 10 minutes to 8 hours. In each method, the number of times of treatment performed on the patient is 1 to several times per day, and the period of the treatment is 1 to 2 days or longer. The mode of the treatment may be "every-other-day treatment", "every-day treatment", and/or "consecutive treatment", and can be selected from these as appropriate.

Regarding stimulation caused by an interference wave for treatment of dysphagia, the output of current from paired electrodes is set in a range of 1 to 10 mA (effective value attained when a 500Ω load resistor is connected). This value is set in a manner linked with or not linked with specification of the sensory threshold.

One pair or two pairs of a positive-side electrode and a negative-side electrode are adhered with the thyroid cartilage set at the center therebetween. The electrodes may be any electrodes that are neither unnecessarily large nor small, and that are thin, have high degree of adherence to the skin, and furthermore, are flexible, so as not to cause discomfort in the patient in a state where the electrodes are adhered to the skin of the patient. If the patient feels discomfort with the electrodes adhered to the skin of the patient, a long-time use of the electrodes is affected. If the degree of adherence of the electrodes is low, and adherence of two or four electrodes in total is uneven, electric resistance via the skin becomes uneven, and this could lead to failure in causing percutaneous flow of intended current.

Within the various conditions as described above, a specific condition of treatment in dysphagia therapy, e.g., carrier frequency, treatment frequency, process output, output mode, and output time, is recorded and saved as data in the dysphagia treatment device. In the dysphagia treatment device, an optimum condition for treatment can be set by use of data of a sensory threshold before the treatment and a sensory threshold after the treatment (measurement of next time).

3. Device

One mode of the device according to the present invention is a dysphagia test device at least provided with means for percutaneously applying stimulation by an interference wave or a pseudo interference wave. The device according to this mode has a function capable of: obtaining a sensory threshold of an individual (patient) through stimulation treatment using the above-mentioned means; recording and saving as data the obtained sensory threshold; and calling the saved data when necessary. As the details of this function, the details explained in the section of the dysphagia test method described above are mutatis mutandis applied. The device according to a preferable mode has a function capable of increasing the output of stimulation automatically or non-automatically, in an inclined manner or stepwise.

A still another mode of the present invention is a device that includes: a function as a device for performing a dysphagia test; and means capable of obtaining a set value of an individual optimum stimulation condition for each patient on the basis of a sensory threshold obtained through the test, and capable of treating dysphagia on the basis of the obtained set value.

The device to be used in a dysphagia test may be a single device. This device may further have a function for setting a condition for stimulation that is caused by an interference wave or a pseudo interference wave and that is optimum for each individual (patient), for treatment of dysphagia. In addition, this device may be a dysphagia treatment device that has a function of treating dysphagia through stimulation caused by an interference wave or a pseudo interference wave.

The dysphagia treatment device having such a complex function includes: means for specifying a sensory threshold for each patient and for recording and saving as data the specified sensory threshold; and means for reading out the sensory threshold saved as the data and for specifying an optimum stimulation output condition for the patient (individual optimum stimulation output condition), wherein the dysphagia treatment device can be operated in a linked manner or in a non-linked manner on the basis of the specified individual optimum stimulation output condition as necessary.

Another mode of the present invention may be a dysphagia treatment device additionally provided with the means regarding the above-described dysphagia test method, and further, if necessary, with the means for specifying the individual optimum stimulation output condition. The dysphagia treatment device itself may have means for confirming a sensory threshold. In this case, as such means, the following means may be selected and incorporated into the dysphagia treatment device: confirmation means for a stimulation output current value, such as an ammeter; stimulation confirmation display means for a subject, such as a push button to be pushed as confirmation display means by the subject when the subject has become aware of an interference wave weak current; means for recording and saving, through the pushing action, the current value as data of the sensory threshold at that time point of the subject; further, means for reading out the recorded and saved data in a time-based manner and for each individual and for displaying the read out data; means for specifying a future individual optimum interference wave stimulation condition on the basis of correlation and the like between the data obtained in the test at this time and history data, and if necessary, statistical data and data, etc. obtained by known dysphagia test means; means for selecting a treatment method in accordance with the present degree of dysphagia from among a plurality of interference wave treatment methods; and the like. The dysphagia treatment device can be adjusted such that operation based on the individual optimum interference wave stimulation condition thus specified can be executed in a linked manner or in a non-linked manner. "Linked" denotes a manner in which a series of operations, linked with data analysis, lead to actual operation of the device, and "non-linked (or not linked)" denotes a manner in which accrual operation of the device is not associated with data analysis.

A system or a device for dysphagia test or dysphagia treatment includes means for recording and saving, during use at least, a sensory threshold that has allowed the patient to become aware of stimulated feeling caused by stimulation. Here, the saved data can be called in a time-based manner, displayed, and compared with saved data and a numerical value in the history. A numerical value for this comparison is displayed and used as a marker for progress of the degree of dysphagia and/or for the degree of improvement. Further, on the basis of this numerical value, an individual optimum interference wave stimulation condition for each patient is set. With this configuration, a system or a device for dysphagia test and dysphagia treatment using an interference wave or a pseudo interference wave is provided.

Verification

Hereinafter, experiments performed in order to confirm the effects attained by the above-described method are described. The experiments were performed under the following conditions.

For each subject, a sensory threshold caused by an interference wave was confirmed. The subjects were healthy individuals not having dysphagia and patients having dysphagia.

Two pairs of electrodes, each pair consisting of a positive-side electrode and a negative-side electrode, were attached in a cross-like shape to the neck of each subject. Also in a method in which one pair of electrodes were attached, an experiment was performed in a similar manner.

With the carrier frequencies set at 2000 Hz and 2050 Hz, an interference wave was applied to each subject such that the treatment frequency (beat frequency) was adjusted to 50 Hz. For interference wave stimulation, a device capable of setting voltage of 0 V to 10 V in 10 to 100 levels was used. For each subject, a current value at the lowest strength at which the subject could become aware of stimulation caused by the device was recorded as the sensory threshold.

In order to confirm correlation between the sensory threshold and the degree of dysphagia, a known dysphagia improvement determination method was used. In this examination, the dysphagia state of each dysphagia patient whose sensory threshold was monitored was determined on the basis of the result of laryngeal elevation delay time (LEDT), which is one of analysis items for radiographic moving image obtained through a videofluoroscopic swallow test.

A videofluoroscopic swallow test is a test for performing evaluation by use of a radioscopic test, and is a technique in which: a person is caused to sit in a wheelchair in a radioscopic room, and to actually take in a liquid, a thickened liquid, a paste, a jelly, or the like which contains barium or the like; and the swallowing function is evaluated. The laryngeal elevation delay time (LEDT), which is an index to be used in the videofluoroscopic swallow test, was obtained by advancing a profile view, frame by frame, for the time period from the leading end of the contrast medium reached the bottom of the pyriform sinus until the larynx elevation became maximum. The shorter (smaller) the LEDT is, the more recovered the swallowing symptom is. As display data, the determined LEDT value was shown.

Under the above-described condition, with respect to a total of 81 healthy individuals (ages 16 to 68) including males and females, the sensory threshold was measured. As a result, the sensory threshold exhibited the distribution as shown in FIG. 1. It was confirmed that the sensory threshold had an average of 1.05 mA, a maximum of 2.18 mA, and a minimum of 0.18 mA. Also when stimulation caused by a pseudo interference wave was applied by use of one pair of electrodes, a result substantially equivalent to that shown in FIG. 1 was obtained.

Next, with respect to three patients (subject) determined as having dysphagia from the result of laryngeal elevation delay time (LEDT), continuous interference wave stimulation was provided every day or at a 3-day interval, for 10 to 30 minutes each time (1 to 3 times/day). The patients were to 87 years of age, and the first-time sensory thresholds (initial data) were 2.61, 2.8, and 2.89 mA, respectively. The numerical values of these sensory thresholds were about twice 1.05 which was the average value of the healthy individuals described above. The first-time LEDT (sec) values of these three patients were 1.567, 0.233, and 0.533, respectively. The treatment was consecutively performed on the three patients 60 times at maximum. In the treatment, each time, the sensory threshold was measured, and data of the measurement result was inputted, recorded, and saved. Using as a reference the sensory threshold obtained through the treatment each time, the treatment condition for the next time was set.

Figure 2:
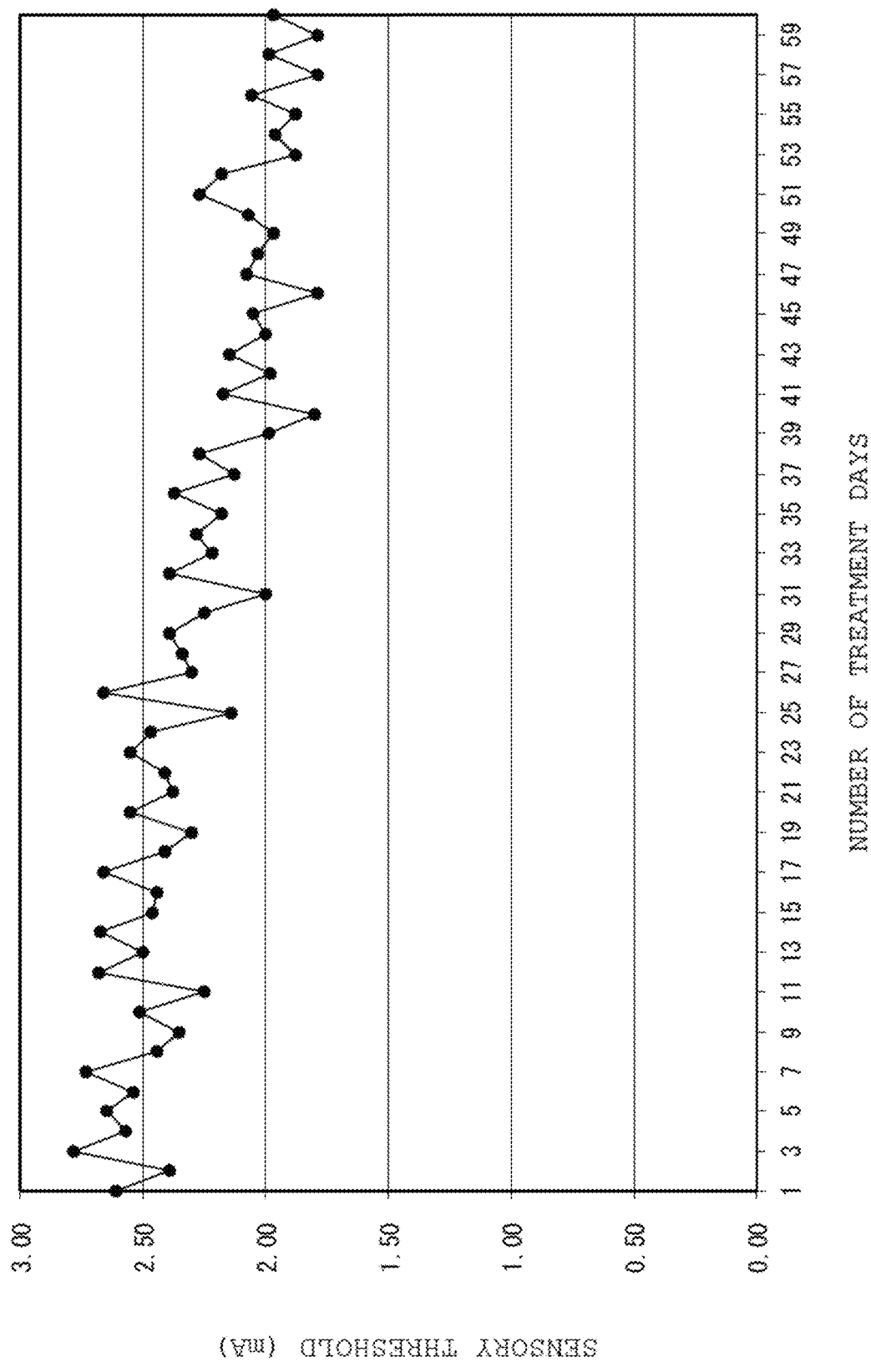
FIG. 2 is a graph showing a measurement result obtained when stimulation caused by an interference wave was applied to subject 1 and the sensory threshold of subject 1 was measured every day, according to the embodiment.
Figure 3:
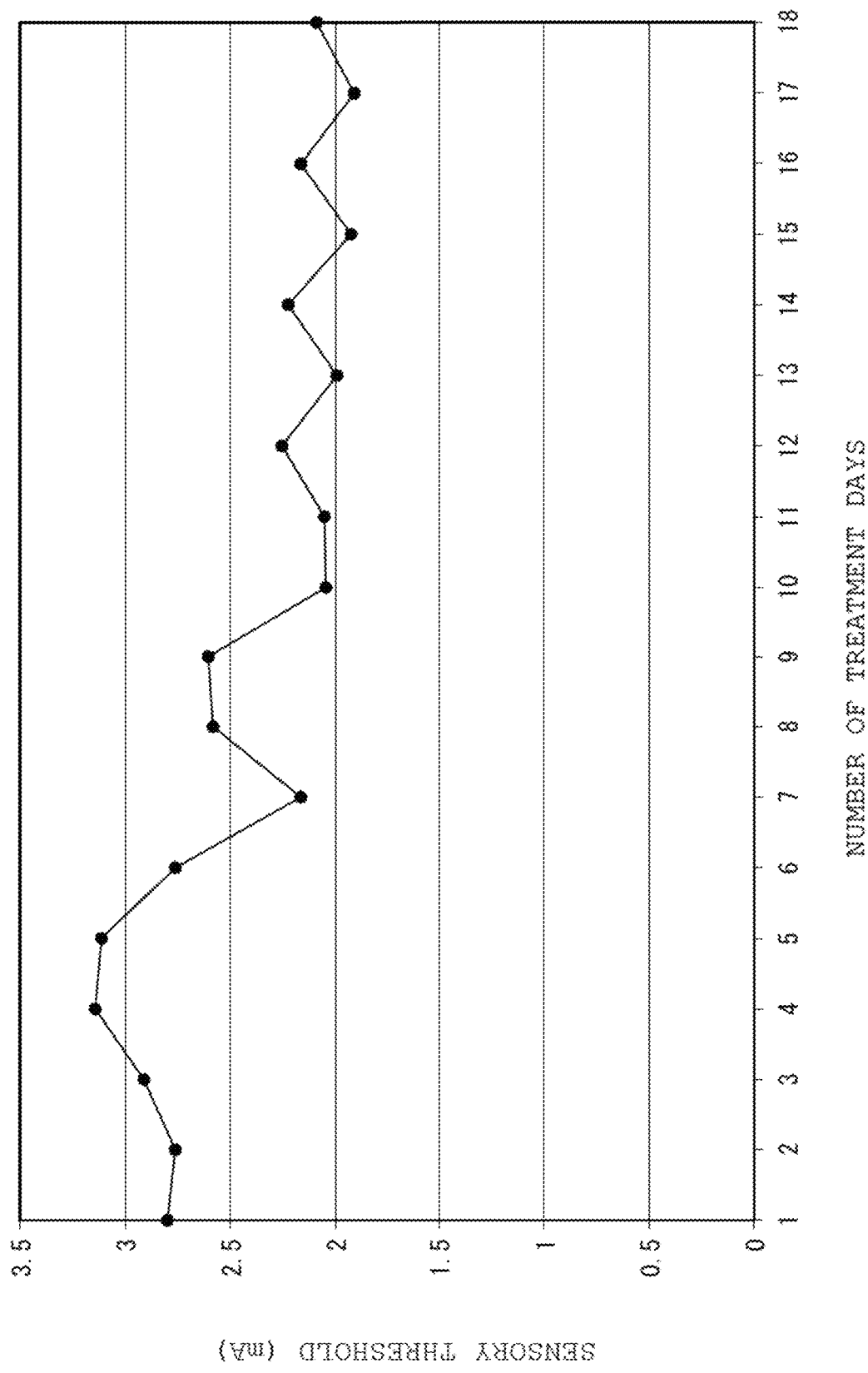
FIG. 3 is a graph showing a measurement result obtained when stimulation caused by an interference wave was applied to subject 2 and the sensory threshold of subject 2 was measured every day, according to the embodiment.
Figure 4:
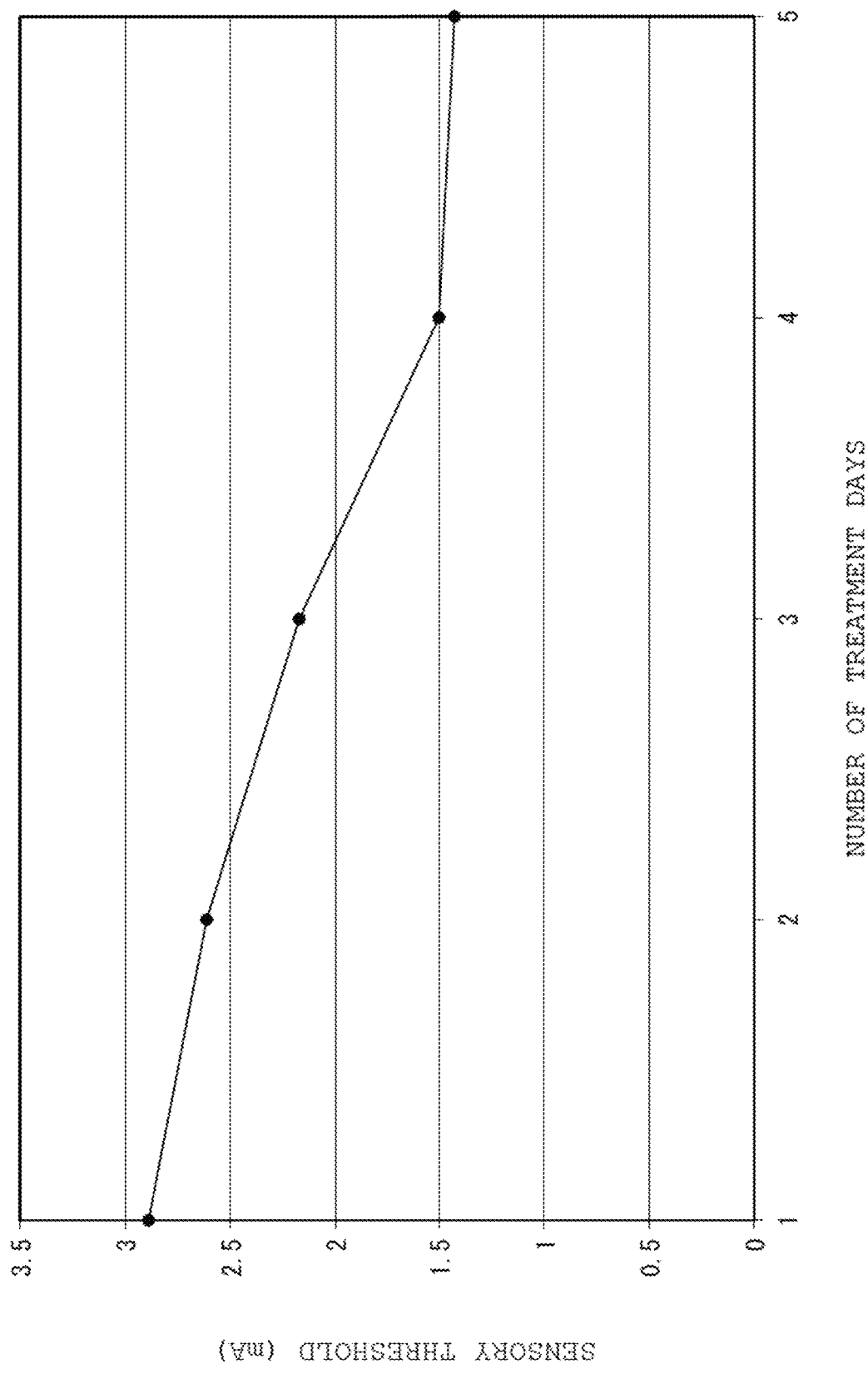
FIG. 4 is a graph showing a measurement result obtained when stimulation caused by an interference wave was applied to subject 3 and the sensory threshold of subject 3 was measured at a 3-day interval, according to the embodiment.

FIG. 2 to FIG. 4 are graphs showing measurement results obtained when stimulation caused by an interference wave was applied to patient subjects 1 to 3 and the sensory thresholds of patient subjects 1 to 3 were measured. The vertical axis represents sensory threshold current (mA), and the horizontal axis represents the number of times of tests. Patient subjects 1, 2 received the test every day, and patient subject 3 received the test at a 3-day interval.

With respect to patient subject 1 (initial value: sensory threshold 2.61 mA, LEDT 1.567 (sec)), the sensory threshold did not become lower than 2.0 mA until the 38th treatment, but showed a tendency of gradual decrease thereafter. At the 39th treatment, the sensory threshold decreased to 2.18 mA, and LEDT decreased to 0.133 (sec), and at the 53rd treatment, the sensory threshold decreased to 1.88 mA. The degree of dysphagia was confirmed by means of the numerical value of LEDT, and the degree of dysphagia was significantly improved before around the 14th treatment.

With respect to patient subject 2 (initial value: sensory threshold 2.8 mA, LEDT 0.233 (sec)), the sensory threshold decreased to 2.16 mA through 7 treatments, and at the 8th treatment, LEDT decreased to 0.066. The degree of dysphagia was sufficiently improved through about 7 treatments.

With respect to patient subject 3 (initial value: sensory threshold 2.89 mA, LEDT 0.533 (sec)), the sensory threshold did not become lower than 2.0 mA until the 3rd treatment. However, the sensory threshold showed a tendency of rapid decrease through the 4th treatment, and at the 5th treatment, the sensory threshold decreased to 1.43 mA. During this time, LEDT decreased to 0.333 (sec) at the treatment of day 5, and the degree of dysphagia was also noticeably improved.

Further, also with respect to one patient (subject) determined as having dysphagia from the result of laryngeal elevation delay time (LEDT), continuous interference wave stimulation was provided at an every day interval, for 10 to 30 minutes each time (1 to 3 times/day). The patient was 91 years of age, and the first-time sensory threshold (initial data) was 1.90 mA. The first-time LEDT (sec) value of this patient was 0.467. The treatment was consecutively performed on this patient, 22 times. In the treatment, each time, the sensory threshold was measured, and data of the measurement result was inputted, recorded, and saved. Using as a reference the sensory threshold obtained through the treatment each time, the treatment condition for the next time was set.

Figure 5:
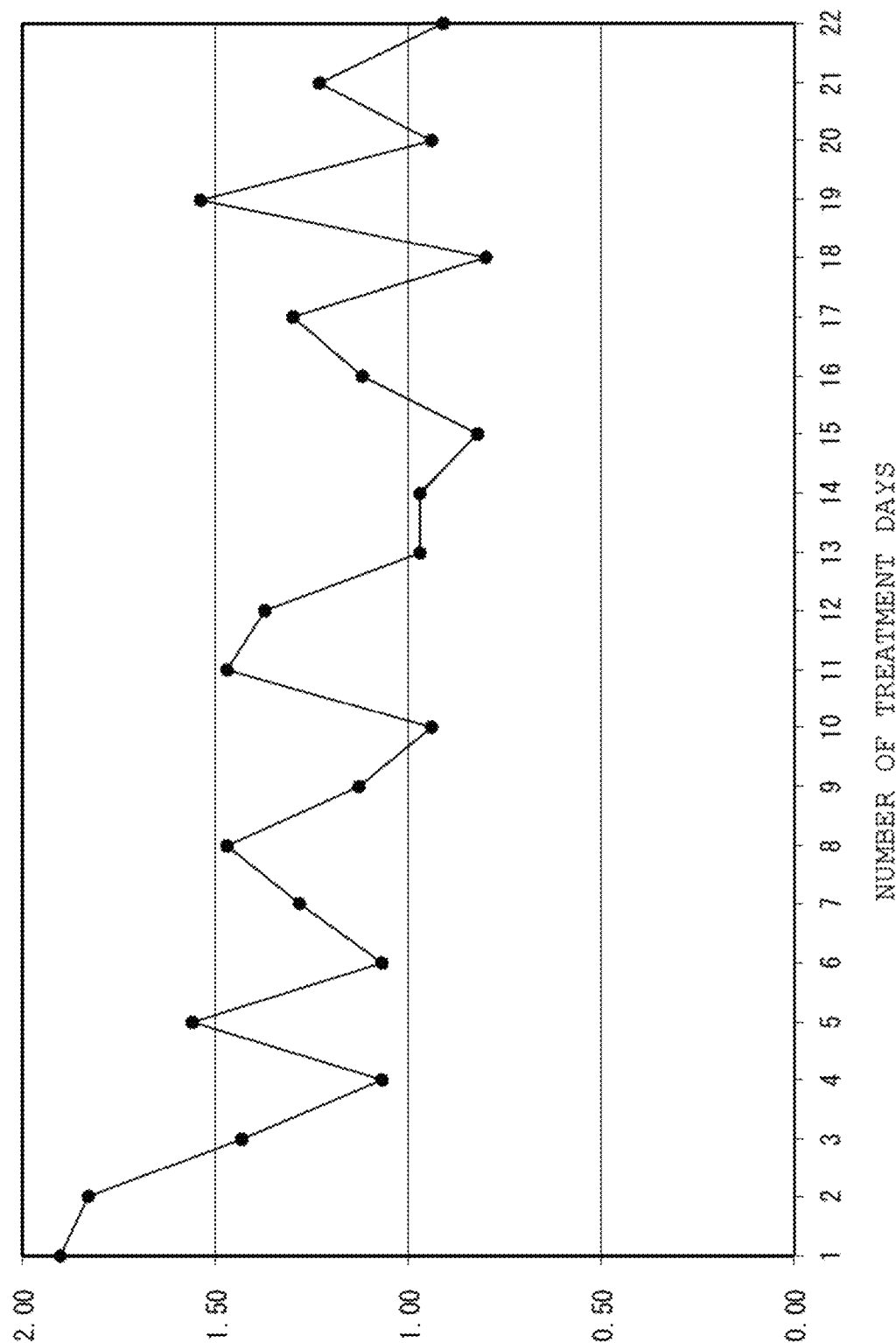
FIG. 5 is a graph showing a measurement result obtained when stimulation caused by an interference wave was applied to subject 4 and the sensory threshold of subject 4 was measured at a 3-day interval, according to the embodiment.

FIG. 5 is a graph showing a measurement result obtained when stimulation caused by an interference wave was applied to a patient subject and the sensory threshold of the patient subject was measured. The patient was 90 years of age, and continuous interference wave stimulation was provided for 20 minutes each time (2 times/day). Also in this patient subject, the sensory threshold showed a tendency of gradual decrease in association with the treatment. At the 21st treatment, LEDT also decreased to 0.167 (sec), and the degree of dysphagia also greatly improved.

Through the results described above, correlation between the degree of dysphagia and the sensory threshold was confirmed. In addition, the effectiveness of consecutively confirming and recording the sensory threshold, and of setting, on the basis of the value, the output value for the next time treatment condition was confirmed. Thus, the dysphagia treatment device can employ a method in which, on the basis of the sensory threshold obtained through the measurement each time, the treatment condition for the next time appropriate for the degree of improvement attained by the treatment of dysphagia is automatically set.

The results described above were obtained through the treatment performed in a system using two pairs of output. Meanwhile, with respect to a system using one pair of output and using continuous interference wave output similar to that described above, and with respect to a system using two pairs consisting of: a system using an intermittent (1-second interval) interference wave only; and a system using an intermittent (1-second interval) interference wave and a non-interference wave, a preliminary experiment was performed several times. As a result, correlation between decrease of the sensory threshold and improvement of the degree of dysphagia was similarly assumed.

Specific Configuration Example of Device

With reference to FIG. 6A to FIG. 10C, a specific configuration example of the dysphagia treatment device is described. The dysphagia treatment device according to the present configuration example has a function for testing dysphagia, and a function for performing treatment of dysphagia in accordance with the test result.

In the present configuration example, step S15 in FIG. 9A corresponds to "step of applying" in the claims, step S12 to S15, S17, and S18 in FIG. 9A corresponds to "step of obtaining" in the claims, step S16 in FIG. 9A corresponds to "step of displaying" in the claim, and step S19 in FIG. 9A corresponds to "step of causing --- to be outputted" in the claim.

Figure 6B:
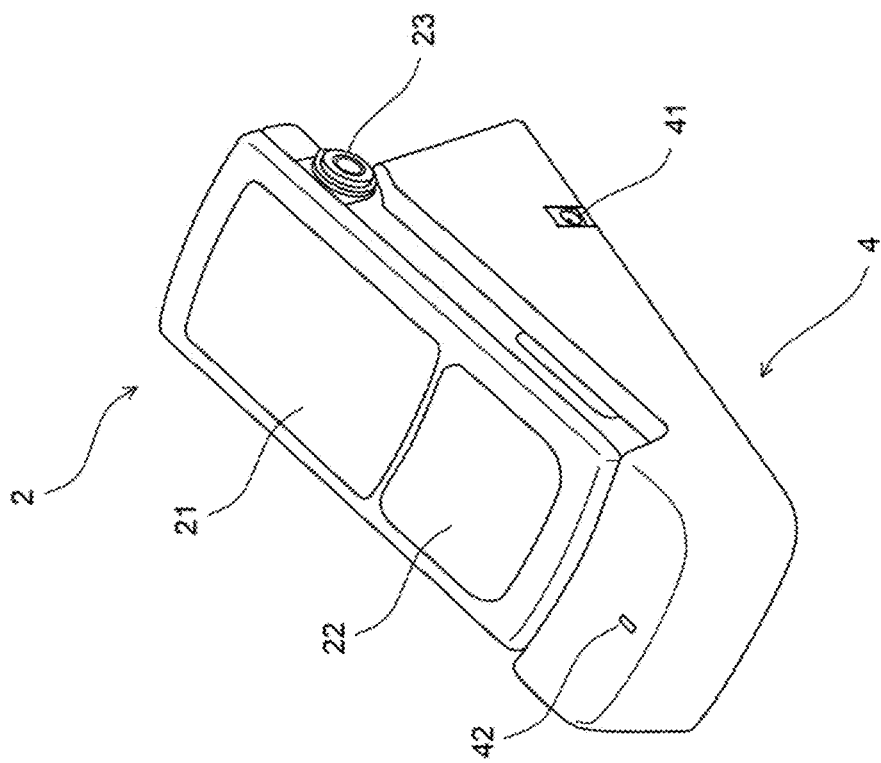
FIG. 6B is a perspective view showing a state where a treatment unit body is mounted to a charger, according to the embodiment.
Figure 6A:
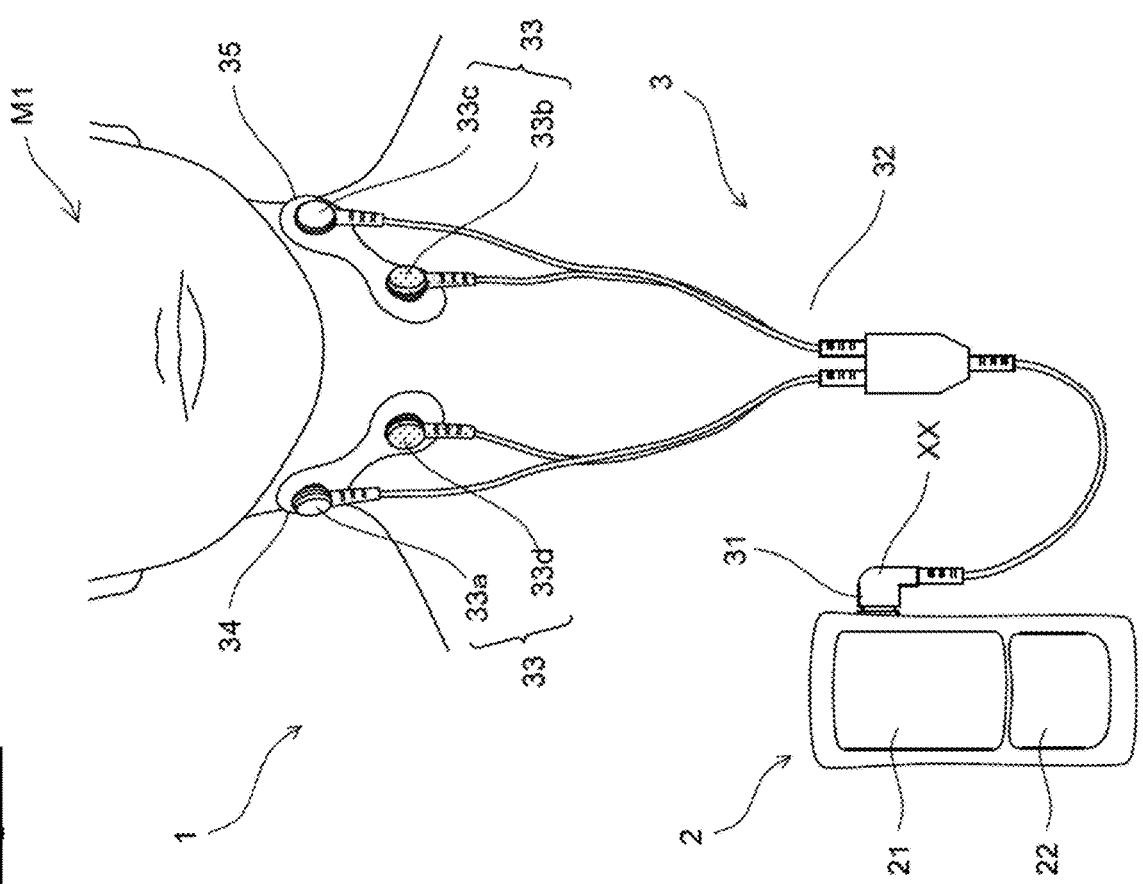
FIG. 6A is a diagram showing an external configuration of a dysphagia treatment device in a state where the dysphagia treatment device is attached to a treated person according to the embodiment.

FIG. 6A is a diagram showing an external configuration of a dysphagia treatment device 1 in a state where the dysphagia treatment device 1 is attached to a treated person M1. FIG. 6B is a perspective view showing a state where a treatment unit body 2 is mounted to a charger 4.

As shown in FIG. 6A, the dysphagia treatment device 1 includes the treatment unit body 2 and a current application unit 3. The treatment unit body 2 includes a display unit 21 and an operation unit 22. The display unit 21 displays the value of a current percutaneously applied by the current application unit 3 to the treated person M1, and information such as a treatment time period set by the operator. The operation unit 22 includes: a key for increasing or decreasing the value of the current percutaneously applied to the treated person M1; a key for setting a treatment time period; and the like. The treatment unit body 2 has a handy size that allows the treatment unit body 2 to be carried while being gripped by a hand.

As shown in FIG. 6B, the treatment unit body 2 is set at the charger 4 to be charged. In FIG. 6B, a power supply cable connected to the charger 4 is omitted, for convenience. The power supply cable is connected to a connector 41 of the charger 4. The charger 4 further includes a lamp 42 indicative of a charge state. As shown in FIG. 6B, when the treatment unit body 2 is set at the charger 4, a receiving connector (not shown) of the treatment unit body 2 is connected to a feeding connector (not shown) of the charger 4. The treatment unit body 2 includes, at a side face thereof, a connector 23 for connecting a connector 31 of the current application unit 3.

As shown in FIG. 6A, the current application unit 3 includes the connector 31, a cable 32, electrodes 33, and pads 34, 35. The connector 31 is connected to the connector 23 of the treatment unit body 2. The cable 32 connects the connector 31 and the electrodes 33 to each other. The electrodes 33 are implemented by two anodes 33a, 33c and two cathodes 33b, 33d. Here, the anode 33a and the cathode 33b are paired to form one pair of electrodes 33, and the anode 33c and the cathode 33d are paired to form one pair of electrodes. The anode 33a and the cathode 33d are mounted to one pad 34, and the anode 33c and the cathode 33b is mounted to the other pad 35.

As shown in FIG. 6A, the two pairs of the electrodes 33 are adhered to the neck such that the anodes 33a, 33c and the cathodes 33b, 33d are arranged in an X-like shape at the neck of the treated person M1. The pads 34, 35 are each formed from a thin and flexible material.

Figure 7:
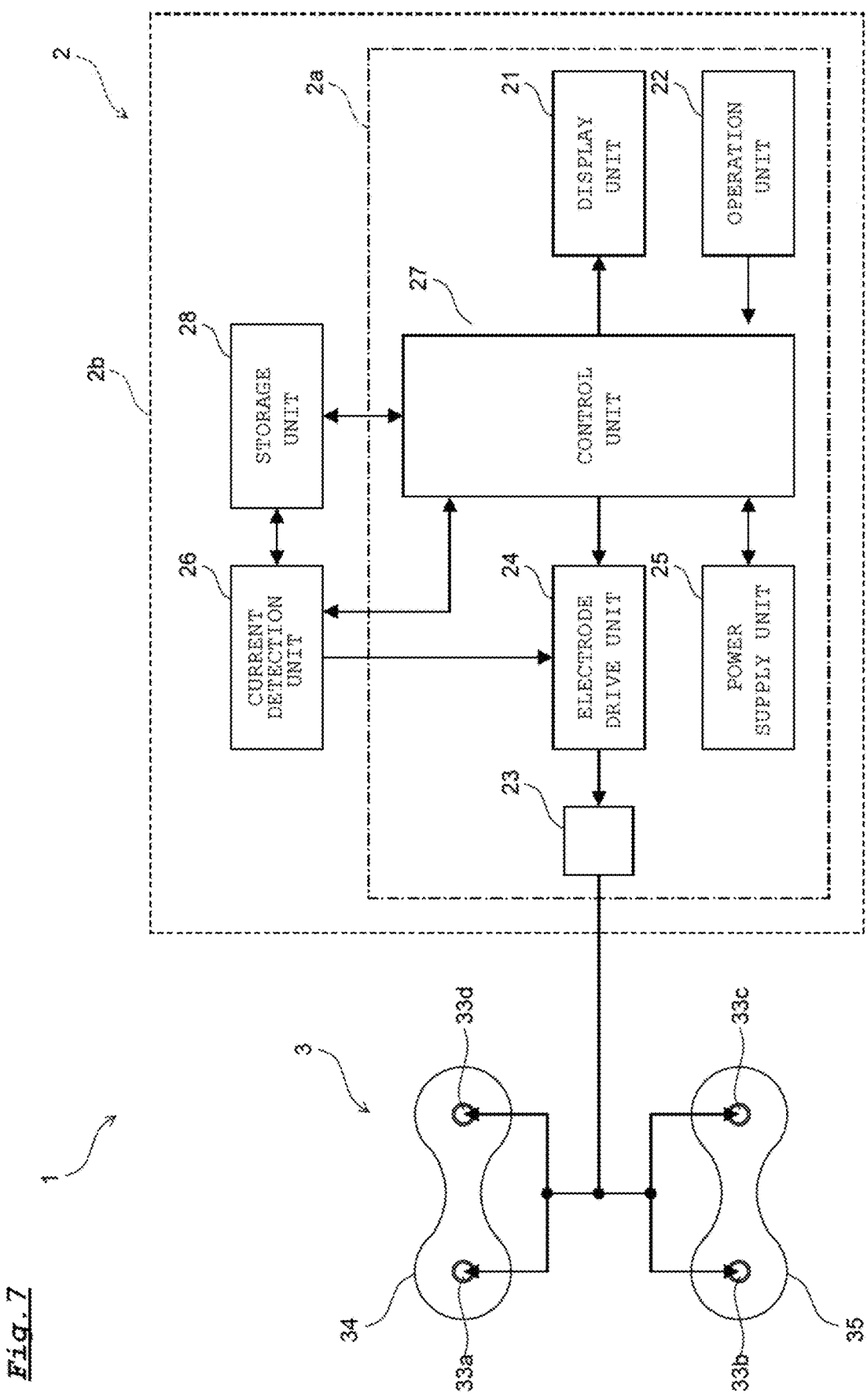
FIG. 7 is a block diagram showing a configuration of the treatment unit body, according to the embodiment.

FIG. 7 is a block diagram showing a configuration of the treatment unit body 2.

In addition to the display unit 21, the operation unit 22, and the connector 23 shown in FIGS. 6A, 6B, the treatment unit body 2 includes an electrode drive unit 24, a power supply unit 25, a current detection unit 26, a control unit 27, and a storage unit 28. A block 2a is a block mainly regarding treatment of dysphagia, and a block 2b is a block mainly regarding dysphagia test. A dysphagia test device that does not perform dysphagia treatment operation has a configuration similar to that of the block 2b. In this dysphagia test device, among processes to be described with reference to FIG. 9A later, only the processes in steps S11 to S18 are performed.

Through control from the control unit 27, the electrode drive unit 24 applies, via the connector 23, voltages of predetermined frequencies to the pair of the anode 33a and the cathode 33b and to the pair of the anode 33c and the cathode 33d respectively. The power supply unit 25 is provided with a rechargeable battery, charges electric power supplied from the charger 4 shown in FIG. 6B, and supplies charged electric power to each unit.

Through control from the control unit 27, the current detection unit 26 measures the current flowing from the electrode drive unit 24 into the anode 33a, 33c, and the cathode 33b, 33d, that is, the current being percutaneously applied to the treated person M1, and stores the measured current value in the storage unit 28.

The control unit 27 is implemented by an arithmetic processing circuit such as a CPU (central processing unit) or the like, and controls each unit according to a control program stored in the storage unit 28. The storage unit 28 includes storage mediums such as a ROM (read only memory) and a RAM (random access memory). The storage unit 28 stores the control program, and also stores various types of information such as the current value detected by the current detection unit 26. The storage unit 28 is also used as a work area for the control unit 27.

FIG. 8A is a schematic diagram showing the waveform of the voltage applied from the paired electrodes 33 (for example, the anode 33a and the cathode 33b). FIG. 8B is a schematic diagram showing the action by the dysphagia treatment device 1 under application of voltage.

As shown in FIG. 8A, the electrode drive unit 24 applies voltage of rectangular wave having a predetermined frequency from the paired electrodes 33 (for example, the anode 33a and the cathode 33b) to the neck of the treated person M1. Here, the rectangular wave oscillates between +Vp and −Vp. The rectangular wave is set at a predetermined duty ratio. The frequency of the rectangular wave (carrier frequency) is set between 500 to 8000 Hz. Preferably, the frequency of the rectangular wave (carrier frequency) is set between 1000 to 4000 Hz, and further preferably between 1500 to 3000 Hz. The applied voltage may not necessarily be of rectangular wave, and may be of sine wave, for example.

Then, when voltage is applied to the neck of the treated person M1, current percutaneously flows toward the superior laryngeal nerve of the treated person M1. Here, if the frequency of the voltage applied from one pair of the electrodes (for example, the anode 33a and the cathode 33b) is made different from the frequency of the voltage applied from the other pair of the electrodes 33 (for example, the anode 33c and the cathode 33d), an interference wave of current is generated, and this interference wave is applied to the superior laryngeal nerve of the treated person M1. Accordingly, the superior laryngeal nerve is stimulated, whereby dysphagia of the treated person M1 is treated.

The frequency of the interference wave (beat frequency, i.e., dysphagia treatment frequency) is a frequency corresponding to the difference in frequencies between the two pairs of the electrodes 33. The frequency of the interference wave is set between 10 to 100 Hz, preferably between 20 to 80 Hz, and further preferably between 30 to 60 Hz.

In the example shown in FIG. 8B, voltage of 2050 Hz is applied from one pair of the electrodes 33 (the anode 33a, the cathode 33b) to the neck of the treated person M1, and voltage of 2000 Hz is applied from the other pair of the electrodes 33 (the anode 33c, the cathode 33d) to the neck of the treated person M1. Accordingly, a current wave of 2050 Hz and a current wave of 2000 Hz advance toward the superior laryngeal nerve, and an interference wave of 50 Hz acts on the superior laryngeal nerve.

If the amplitude (strength) of voltage to be applied to each of the pairs of the electrodes is caused to vary, the amplitude of the current wave is varied, and accordingly, the strength of the interference wave acting on the superior laryngeal nerve is also varied. Therefore, through adjustment of the amplitude of voltage to be applied to each of the pairs of the electrodes, stimulation to be applied to the superior laryngeal nerve of the treated person M1 can be adjusted to a strength that is appropriate for the treatment. The voltages to be applied to the respective pairs of the electrodes are set to have the same amplitude with each other.

FIG. 9A is a flow chart showing a process for setting a current value to be used in the treatment (treatment current value). FIG. 9B is a diagram showing a configuration of a screen to be displayed on the display unit 21 of the treatment unit body 2 and a configuration of the operation unit 22 thereof.

First, with reference to FIG. 9B, the display unit 21 includes a voltage scale region 211, an indicator region 212, a current value region 213, a timer region 214, and a battery region 215. The display unit 21 is provided with a liquid crystal display, for example.

In the voltage scale region 211, four scales are displayed, each scale being for indicating, by a digit, the level of voltage to be applied from the electrodes 33 to the neck. That is, in the voltage scale region 211, four scales, i.e., 0, 5, 10, and 15, are displayed so as to be arranged vertically at equal intervals. In the indicator region 212, an indicator variable from the height position of scale 0 to the height position of scale 15 is displayed. The height of the indicator is varied in accordance with the level of the voltage being applied from the electrodes 33 to the neck, i.e., in accordance with the amplitude of the rectangular wave shown in FIG. 8A.

In the current value region 213, the current value measured by the current detection unit 26 shown in FIG. 7, i.e., the effective value of the value of the current being percutaneously applied from the electrodes 33 is displayed. In the current value region 213, mA (milliampere), which is the unit of the current value, is also displayed. In the timer region 214, a treatment time period set by the operator such as a doctor is displayed. In the battery region 215, electric power remaining in the power supply unit 25 shown in FIG. 7 is displayed.

The operation unit 22 includes a power supply key 221, a timer key 222, an UP key 223, and a DOWN key 224. The power supply key 221 is used for activation and stop of the treatment unit body 2. The timer key 222 is used for setting a treatment time period. The UP key 223 and the DOWN key 224 are used for setting the treatment time period and adjusting the voltage value. Each key is implemented by a mechanical push key which causes a click feeling when pressed, for example.

When a treatment time period is to be set, the operator presses the timer key 222. Accordingly, a default time period is displayed in the timer region 214. The operator can extend the treatment time period by operating the UP key 223, and can shorten the treatment time period by operating the DOWN key 224. Then, after adjusting the treatment time period to a desired time period, the operator presses the timer key 222 again. As a result, the time period displayed in the timer region 214 at that timing is set as the treatment time period.

Next, with reference to FIG. 9A, a process for setting a current value (treatment current value) to be used in the treatment is described. This process is performed after the above-described treatment time period has been set. The process shown in FIG. 9A is performed by the control unit 27 shown in FIG. 7.

In the process for setting the treatment current value, the UP key 223 is used in order to raise the voltage to be applied from the electrodes 33 to the neck, and the DOWN key 224 is used in order to lower the voltage to be applied from the electrodes 33 to the neck. When the UP key 223 is operated in a state where the level of the applied voltage is at the maximum value, the control unit 27 ignores this operation, and when the DOWN key 224 is operated in a state where the level of the applied voltage is at the minimum value (zero), the control unit 27 ignores this operation.

As shown in FIG. 6A, when two pairs of the electrodes are attached to the neck of the treated person M1, then, power is supplied, and then, a treatment time period is set as described above (S11), the control unit 27 determines whether the UP key 223 or the DOWN key 224 of the operation unit 22 has been operated (S12).

Immediately after activation of the treatment unit body 2, voltage is not being applied from the electrodes 33, and thus, the control unit 27 determines whether the UP key 223 has been operated, only (S12). When the UP key 223 has been operated (S12: YES), the control unit 27 determines whether the operation at this time is an operation performed for the first time after the power has been supplied (S13). When the operation at this time is an operation performed for the first time (S13: YES), the control unit 27 starts counting time by a built-in timer (S14). Then, in accordance with the operation performed on the UP key 223, the control unit 27 raises the output voltage from the electrodes 33 by one level (S15). Accordingly, current flows from the neck of the treated person M1 toward the superior laryngeal nerve. The control unit 27 obtains the measurement value of this current (current value Im) from the current detection unit 26 shown in FIG. 7, and causes the display unit 21 to display the obtained measurement value (S16). Accordingly, the measured current value Im is displayed in the current value region 213 shown in FIG. 9B.

Then, the control unit 27 determines whether a time T at which the counting time started in step S14 has reached a time Ts determined in advance (S17). The time Ts is set to about one minute, for example. When the time T has not yet reached the time Ts (S17: NO), the control unit 27 returns the process to step S12, and further determines whether the UP key 223 or the DOWN key 224 has been operated. When the UP key 223 or the DOWN key 224 has been operated (S12: YES), since the operation at this time is not an operation performed for the first time (S13: NO), the control unit 27 raises or lowers the output voltage of the electrodes 33 in accordance with the operation performed on the UP key 223 or the DOWN key 224 (S15). Accordingly, the current that flows is increased or decreased, and the current value Im displayed in the current value region 213 shown in FIG. 9B is varied (S16).

In this manner, until the time T reaches the time Ts (S17), the control unit 27 raises or lowers the output voltage of the electrodes 33 in accordance with the operation performed on the UP key 223 or the DOWN key 224 (S12 to S15). Accordingly, the current value Im displayed in the current value region 213 shown in FIG. 9B is varied (S16).

The operator such as a doctor operates the UP key 223 or the DOWN key 224 to adjust the output level of the electrodes 33 to the minimum voltage level at which the treated person M1 perceives stimulation caused by the interference wave. More specifically, while the operator is varying the output level by operating the UP key 223 or the DOWN key 224, if the treated person M1 perceives stimulation caused by the interference wave, the treated person M1 makes notification thereof. Through this operation, the operator searches the minimum voltage level at which the treated person M1 perceives stimulation caused by the interference wave. Then, when the search has ended, the operator ends operating the UP key 223 or the DOWN key 224, and waits for the time T to reach the time Ts. The time Ts is a period for searching and fixing a sensory threshold Is for the treated person M1.

Thereafter, when the time T has reached the time Ts (S17: YES), the control unit 27 ends counting the time T, and obtains the current value Im displayed on the display unit 21 at that time point, as the sensory threshold Is at which the treated person M1 becomes aware of percutaneous stimulation (S18). The obtained sensory threshold Is is already displayed in the current value region 213 of the display unit 21 in step S16. Then, on the basis of this sensory threshold Is, the control unit 27 sets a treatment current value It for dysphagia for the treated person M1 (S19).

Here, the treatment current value It is set to a current value obtained by lowering, by one level, the output level of the two pairs of the electrodes 33 at the obtainment of the sensory threshold Is, for example. In this case, in step S19, a process of lowering the output level of the two pairs of the electrodes 33 by one level is performed. By slightly lowering the treatment current value It from the sensory threshold Is, it is possible to effectively apply percutaneous stimulation for dysphagia treatment to the treated person M1, while suppressing discomfort caused by the stimulation.

The treatment current value It may be set to the sensory threshold Is, for example. In this case, in step S19, the output level of the two pairs of the electrodes 33 is maintained. Then, percutaneous stimulation for dysphagia treatment can be more effectively applied to the treated person M1.

Alternatively, the treatment current value It is set to a current value obtained by raising by one level the output level of the two pairs of the electrodes 33 at the obtainment of the sensory threshold Is, for example. In this case, in step S19, a process of raising the output level of the two pairs of the electrodes 33 by one level is performed. By slightly raising the treatment current value It from the sensory threshold Is, it is possible to further effectively apply percutaneous stimulation for dysphagia treatment to the treated person M1.

Thereafter, the control unit 27 causes the storage unit 28 shown in FIG. 7 to store the treatment current value It as index information based on the sensory threshold (S20). Accordingly, the process for setting the treatment current value It ends. Thereafter, the dysphagia treatment device 1 goes on with treatment operation using the treatment current value It. As described above, in the treatment operation, a process of repeating application or non-application of an interference wave to the superior laryngeal nerve, a process of continuously applying an interference wave to the superior laryngeal nerve, and the like are performed.

In step S20, the treatment current value It is stored in the storage unit 28, as index information based on the sensory threshold. However, the sensory threshold Is itself obtained at the timing when the determination in step S17 has become YES may be stored in the storage unit 28, as the index information based on the sensory threshold.

In a case where the treatment current value It is raised or lowered relative to the sensory threshold Is, a current value (treatment current value) is measured by the current detection unit 26 shown in FIG. 7 again, and the measured current value is stored in the storage unit 28, as the index information based on the sensory threshold in step S20. Alternatively, on the basis of the sensory threshold Is, the control unit 27 may calculate a current value realized when the output level of the electrodes 33 is lowered by one level, and may store the calculated current value in the storage unit 28, as the index information based on the sensory threshold.

It should be noted that the sensory threshold Is obtained in step S18 is being displayed in the current value region 213 shown in FIG. 9B, continuously from the time point when the display has been updated in the process in the immediately-preceding step S16. Then, when the treatment current value It is set in step S19, the display in the current value region 213 is updated to this treatment current value It, accordingly. In this case, the operator understands either the sensory threshold Is before the display is changed or the treatment current value It after the display is changed, as the index information based on the sensory threshold. However, the difference between the sensory threshold Is and the treatment current value It is, at most, only a slight difference in the current value realized when the output level of the electrodes 33 is varied by one level. Thus, there is no big difference whether the sensory threshold Is or the treatment current value It is understood as the dysphagia evaluation information. Each of the sensory threshold Is and the treatment current value It can be used as the index information based on the sensory threshold.

Figure 10B:
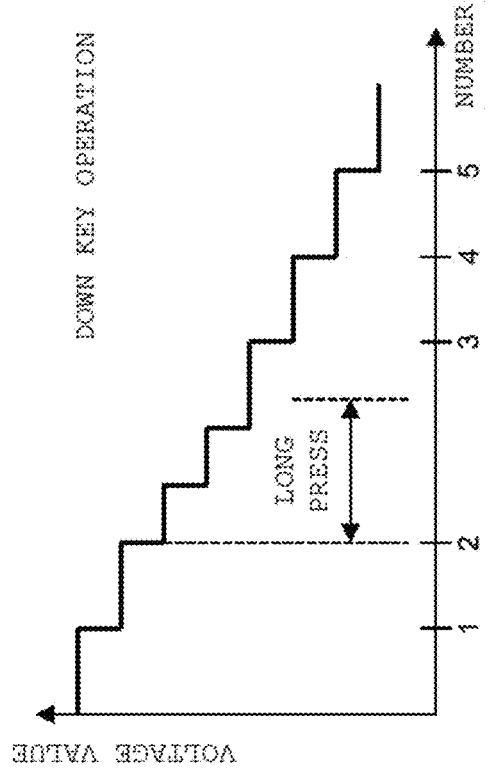
FIGS. 10A and 10B are schematic diagrams respectively showing variation of the output level of electrodes realized when an UP key and a DOWN key are operated, according to the embodiment.
Figure 10A:
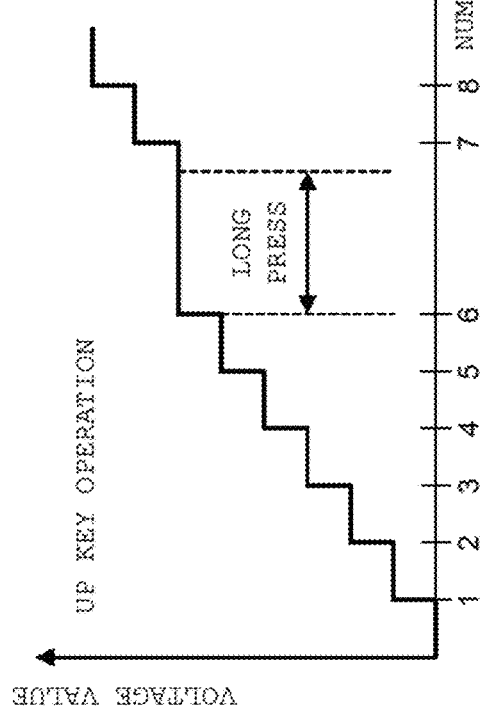

FIGS. 10A and 10B are schematic diagrams showing variation of the output level of the electrodes 33 realized when the UP key 223 and the DOWN key 224 are operated, respectively.

As shown in FIG. 10A, the output level of the electrodes 33 is raised stepwise by one level each time the UP key 223 is pressed. It should be noted that even if the UP key 223 is long pressed, the output level of the electrodes 33 is raised only by one level. The "one level" is set to a predetermined voltage value in advance.

As shown in FIG. 10B, the output level of the electrodes 33 is lowered stepwise by one level each time the DOWN key 224 is pressed. It should be noted that if the DOWN key 224 is long pressed, the output level of the electrodes 33 is consecutively lowered one level by one level. The "one level" is the same as the "one level" realized when the UP key 223 is operated. In this manner, while the DOWN key 224 is long pressed, the output level of the electrodes 33 is controlled so as to be consecutively lowered. Thus, discomfort of stimulation caused by too high an output level can be quickly eliminated.

Figure 10C:
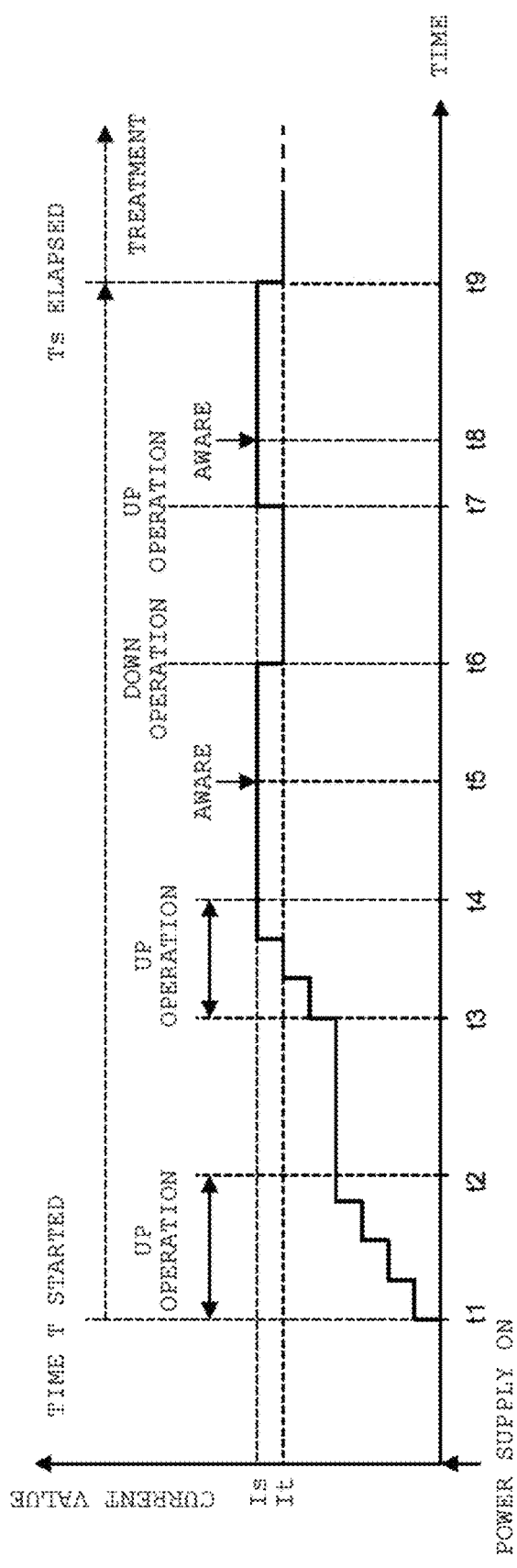
FIG. 10C is a schematic time chart showing variation of the current value until the treatment current value is set, according to the embodiment.

FIG. 10C is a schematic time chart showing variation of the current value until the treatment current value It is set. This time chart is the time chart of a case where the treatment current value It is lowered by one level relative to the sensory threshold Is.

In this example, from time t1 to time t2, the operator performs operation on the UP key 223 four times. As a result, the output level of the electrodes 33 is raised by four levels, and associated therewith, the value of the flowing current is raised stepwise by four levels. Since the operation on the UP key 223 at time t1 is an operation performed for the first time, counting of the time T is started at time t1.

Then, from time t3 to time t4, the operator further performs operation on the UP key 223 three times, and associated therewith, the value of the flowing current is raised stepwise by three levels. Due to this rise of the current value, the treated person M1 becomes aware of, at time t5, percutaneous stimulation to the superior laryngeal nerve, etc., and the treated person M1 makes notification thereof. In response to this, the operator performs operation on the DOWN key 224 once, and associated therewith, the value of the flowing current is lowered stepwise by one level.

Then, from time t6 to time t7, there is no notification by the treated person M1 indicating that the treated person M1 has become aware of stimulation, and thus, at time t7, the operator performs operation on the UP key 223 once, and associated therewith, the value of the current flowing to the superior laryngeal nerve, etc. is raised stepwise by one level. Accordingly, at time t8, the treated person M1 makes notification that the treated person M1 has become aware of stimulation, and thus, the operator determines that the current value at this time is the sensory threshold, and stops performing further UP or DOWN operation.

Then, at time t9 when the time T has reached the time Ts, the current value at that time is obtained as the sensory threshold Is. At the same time, the output of the electrodes 33 is lowered by one level by the control unit 27, and the treatment current value It is set. Thereafter, until the treatment time period set by the operator elapses, treatment control using the treatment current value It is performed. Then, when the treatment time period has elapsed, output of the electrodes 33 is stopped, and treatment for the treated person M1 ends.

In FIG. 10C, the current value is raised and lowered stepwise in a predetermined variation width, through operation performed on the UP key 223 and the DOWN key 224. However, the variation width is not uniform for all treated persons, and is different for each treated person. That is, the resistance value at the time when voltage is applied to the neck could vary depending on the fullness, skeleton, or the like of the neck. Thus, the variation width of the current value when the output of the electrodes 33 is varied by one level is different for each treated person, depending on the resistance value of the neck of the treated person. Therefore, even in a case where treated persons have the same dysphagia level, the time charts shown in FIG. 10C are not necessarily the same with each other, and the number of times of UP or DOWN operation and the variation of the current value associated therewith could be different from each other, depending on the resistance value of the neck.

Figure 11B:
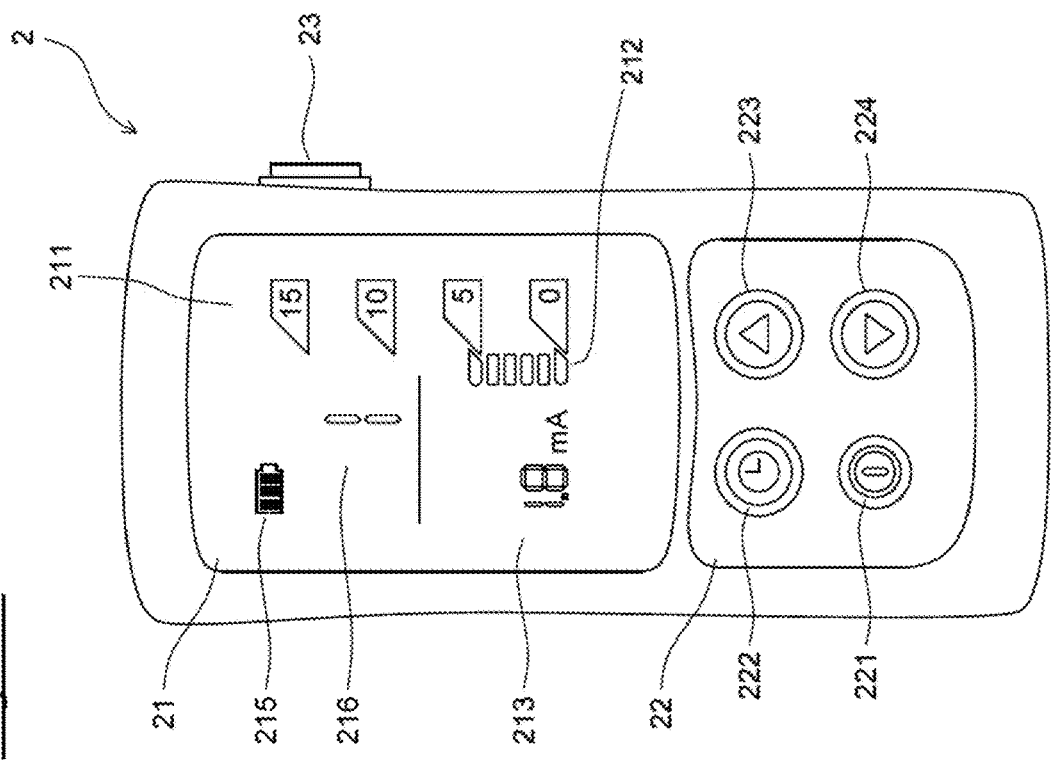
FIG. 11B is a diagram showing a display example of history information according to the embodiment.
Figure 11A:
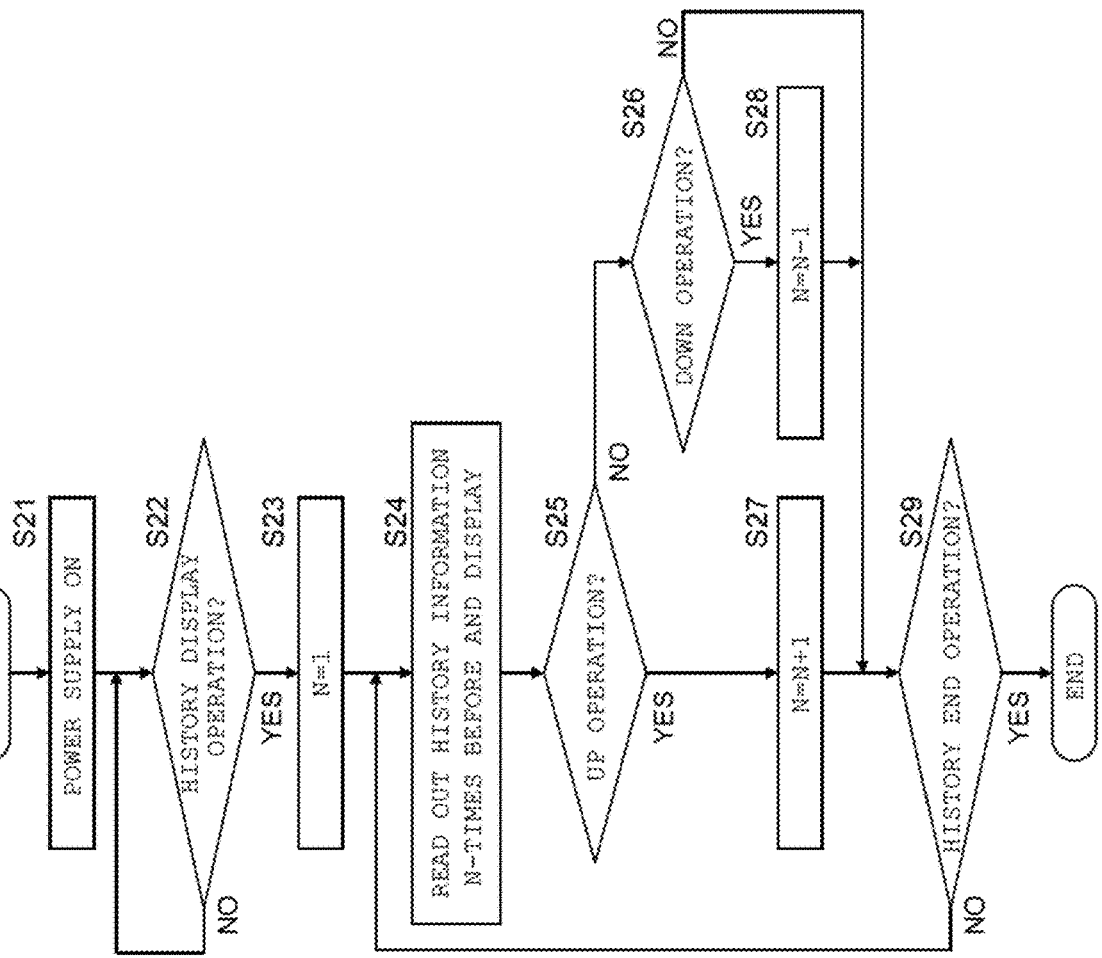
FIG. 11A is a flow chart showing a history information displaying process according to the embodiment.

FIG. 11A is a flow chart showing a history information displaying process.

In the treatment using the dysphagia treatment device 1, for the treatment of each time, the treatment current value It is stored in the storage unit 28 as the index information for dysphagia, in step S20 shown in FIG. 9A. At that time, together with the treatment current value It, the output value (voltage level) of the electrodes 33 at the obtainment of the treatment current value It is stored in the storage unit 28. These pieces of information are associated with the temporal order of the storage process and are sequentially stored in the storage unit 28. The operator can cause, as appropriate, the display unit 21 to display the history information (index information, voltage level) stored in the storage unit 28.

With reference to FIG. 11A, after power is supplied to the treatment unit body 2 (S21), the control unit 27 determines whether operation for displaying past index information has been performed by the operator (S22). This operation is an operation of simultaneously pressing the DOWN key 224 and the timer key 222, for example. When this operation has been performed (S22: YES), the control unit 27 sets 1 as a variable N (S23), reads out history information (index information, voltage level) of N-times before (here, 1-time before) from the storage unit 28, and causes the display unit 21 to display the read history information (S24).

FIG. 11B is a diagram showing a display example of the history information at this time. Here, the index information (current value) based on the sensory threshold obtained in the treatment of 1-time before is displayed in the current value region 213 of the display unit 21. In addition, the level of voltage applied from the electrodes 33 at the obtainment of this index information is displayed in the indicator region 212 of the display unit 21. Further, in the display unit 21, an order region 216 indicative of the temporal order of the history information is allocated instead of the timer region 214. In the order region 216, how many times before the displayed history information was obtained is indicated. In the example shown in FIG. 11B, "1" indicating that the history information was obtained in the treatment of 1-time before is shown.

With reference back to FIG. 11A, next, the control unit 27 determines whether operation on the UP key 223 or operation on the DOWN key 224 has been performed (S25, S26). When operation on the UP key 223 has been performed (S25: YES), the control unit 27 add 1 to the variable N (S27), and when operation on the DOWN key 224 has been performed (S26: YES), the control unit 27 subtracts 1 from the variable N (S28). Then, the control unit 27 determines whether operation for ending display of the history information has been performed by the operator (S29). This operation is again an operation of simultaneously pressing the DOWN key 224 and the timer key 222, for example. When the determination in step S29 is NO, the control unit 27 returns the process to step S24.

In step S24, the control unit 27 reads out history information of N-times before, and causes the display unit 21 to display the read history information. Here, since the variable N has been updated in step S27 or S28, the process in step S24 is performed on the basis of the updated variable N. For example, when 1 has been added to the variable N in step S27, the variable N is 2. In this case, in step S24, history information stored in the treatment of 2-times before is read out from the storage unit 28, and is displayed on the display unit 21. Accordingly, "2" is displayed in the order region 216 shown FIG. 11B, and the index information (current value) and the voltage level obtained in the treatment of 2-times before are displayed in the current value region 213 and the indicator region 212, respectively.

Thus, the operator can refer to the index information and the voltage level obtained in the treatment of a desired number of times before, by operating the UP key 223 and the DOWN key 224. On the basis of the index information referred to, the operator can understand the degree of improvement of dysphagia and the progress degree of the improvement. Accordingly, appropriate treatment can be provided to the treated person M1.

Effect

According to the dysphagia treatment device 1 described above, the following effect can be exhibited.

The index information based on the sensory threshold at which the treated person M1 becomes aware of percutaneous stimulation is displayed on the display unit 21, as an evaluation index for dysphagia. Thus, the operator can evaluate the state of dysphagia of the treated person M1 on the basis of the outputted index information.

The treatment current value It is adjusted in accordance with the level of dysphagia of the treated person M1. Thus, stimulation appropriate for the level of dysphagia of the treated person M1 can be percutaneously applied to the superior laryngeal nerve, etc. of the neck of the treated person M1, and thus, treatment of dysphagia can be effectively carried out.

A method is used in which frequencies of currents respectively applied from two pairs of the electrodes 33 are made different from each other, whereby an interference wave caused by these current is percutaneously applied to the superior laryngeal nerve, etc. located at the depth of the neck of the treated person M1. Accordingly, the test and treatment of dysphagia can be effectively carried out while the load to the treated person M1 is reduced.

In the test and treatment of dysphagia, the level of stimulation to be applied to the superior laryngeal nerve, etc. of the treated person M1 can be adjusted by operating the UP key 223 and the DOWN key 224 shown in FIG. 11B. Thus, the operator can carry out the test and treatment of dysphagia smoothly and in a simple manner.

As shown in FIG. 10C, when the UP key 223 and the DOWN key 224 is operated, the level of current to be applied is varied stepwise. Since the current value is varied stepwise, the operator can, after operating the UP key 223 and the DOWN key 224, monitor response of the treated person M1 at that current value, and can wait for notification from the treated person M1. Accordingly, the operator can carry out the search of the sensory threshold Is smoothly.

As shown in FIG. 10C, in the test of dysphagia, when the elapsed time T, from the time point at which operation of applying stimulation by an interference wave to the superior laryngeal nerve, etc. has started, has reached a predetermined threshold time Ts, the current value at that time is obtained as the sensory threshold Is, and the process is shifted to the treatment. Thus, the operator can perform searching of the sensory threshold while changing the current value during the threshold time Ts, and when the searching of the sensory threshold is completed, the operator can shift the process to the treatment based on the sensory threshold Is, without doing any further operation.

As shown in FIG. 11B, when operation for displaying history is performed, the dysphagia index information (current value) and the voltage level obtained in a past treatment are displayed on the display unit 21. Thus, by referring to the past index information, the operator can understand the degree of improvement of dysphagia and the progress degree of the improvement in the treated person. Accordingly, the operator can provide appropriate treatment to the treated person.

In the state shown in FIG. 11B, when the UP key 223 or the DOWN key 224 is operated, past index information to be displayed on the display unit 21 is shifted in a temporal order. Thus, the operator can smoothly refer to desired past index information through simple operation.

As shown in steps S18, S19 in FIG. 9A, linked with the fact that the sensory threshold Is has been obtained as a result of operation through the operation unit 22, the treatment current value It for the treatment is automatically set. Accordingly, work of setting the treatment current value It with reference to the sensory threshold Is can be omitted, and operativity and convenience of the dysphagia treatment device 1 can be enhanced.

Modification 1

FIG. 12A is a flow chart showing a mode setting process according to Modification 1. FIG. 12B is a flow chart showing a process for setting the treatment current value according to Modification 1.

In Modification 1, the operator can select as desired a mode for setting the treatment current value It in step S19 shown in FIG. 9A, from among three modes. Here, a mode A is a mode for setting the sensory threshold Is as it is, as the treatment current value It, and a mode B and a mode C are modes for setting current values respectively obtained by lowering and raising by one level relative to the sensory threshold Is, as the treatment current value It.

With reference to FIG. 12A, after power is supplied (S31), the control unit 27 determines whether a predetermined mode setting operation has been performed on the operation unit 22 (S32). When this operation has been performed (S32: YES), the control unit 27 causes the display unit 21 to display a mode setting screen (S33). The operator performs operation on the UP key 223 and the DOWN key 224, to select a desired mode, and then, performs operation for fixing the mode setting. Then, when the mode setting is completed (S34: YES), the control unit 27 stores the set mode as the mode for the process of step S19 (S35). Then, the mode setting ends.

In Modification 1, the process shown in FIG. 12B is performed in step S19 shown in FIG. 9A. The control unit 27 determines which one among the modes A to C is the mode set by the operator. In a case where the operator has not set any mode, the mode B is set as default, for example.

When the set mode is the mode A (S41: YES), the control unit 27 sets a voltage level Vt of the electrodes 33 to a voltage level Vs at the obtainment of the sensory threshold Is (S42). Accordingly, the sensory threshold Is itself is set as the treatment current value It. When the set mode is the mode B (S41: NO, S43: YES), the control unit 27 sets the voltage level Vt of the electrodes 33 to a voltage value obtained by lowering by one level the voltage level Vs at the obtainment of the sensory threshold Is (S44). Accordingly, a current value lowered by one level relative to the sensory threshold Is is set as the treatment current value It. When the set mode is the mode C (S41: NO, S43: NO), the control unit 27 sets the voltage level Vt of the electrodes 33 to a voltage value obtained by raising by one level the voltage level Vs at the obtainment of the sensory threshold Is (S45). Accordingly, a current value raised by one level relative to the sensory threshold Is is set as the treatment current value It.

According to Modification 1, the operator can select a mode for setting the treatment current value It as appropriate. Thus, the degree of freedom when setting the treatment current value It can be enhanced, and the operator can provide the treatment to the treated person in a mode that the operator considers appropriate for the treatment.

In Modification 1, as the mode for setting the treatment current value It, three modes i.e., the modes A to C, are selectable. However, the selectable modes are not limited thereto. For example, two modes among the modes A to C may be selectable, and further, another mode may be selectable. ΔV in steps S44, S45 shown in FIG. 12B may not be necessarily the same as the variation width of the voltage level in the process of searching the sensory threshold Is, i.e., the variation width per step in FIGS. 10A, 10B.

Modification 2

FIG. 12C is a flow chart showing a process for setting the treatment current value according to Modification 2. In Modification 2, step S20 shown in FIG. 9A is changed to step S20'. That is, in step S20', the control unit 27 causes the storage unit 28 to store the sensory threshold Is obtained in step S18 as it is. Thus, the operator can refer to the sensory threshold Is itself as the index information in past treatment, through the above operation described with reference to FIG. 11B.

Other Modifications

Figure 13B:
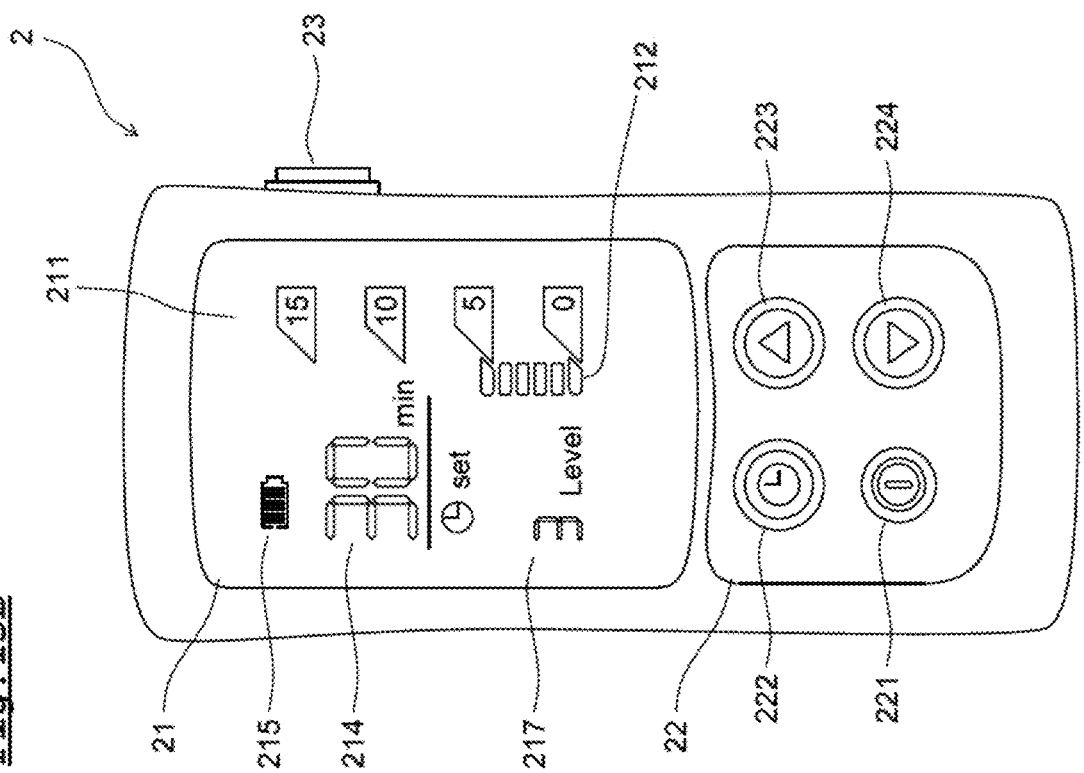
FIGS. 13A and 13B are diagrams each showing a configuration of a screen to be displayed on the display unit of the treatment unit body and a configuration of the operation unit thereof, according to other modifications.
Figure 13A:
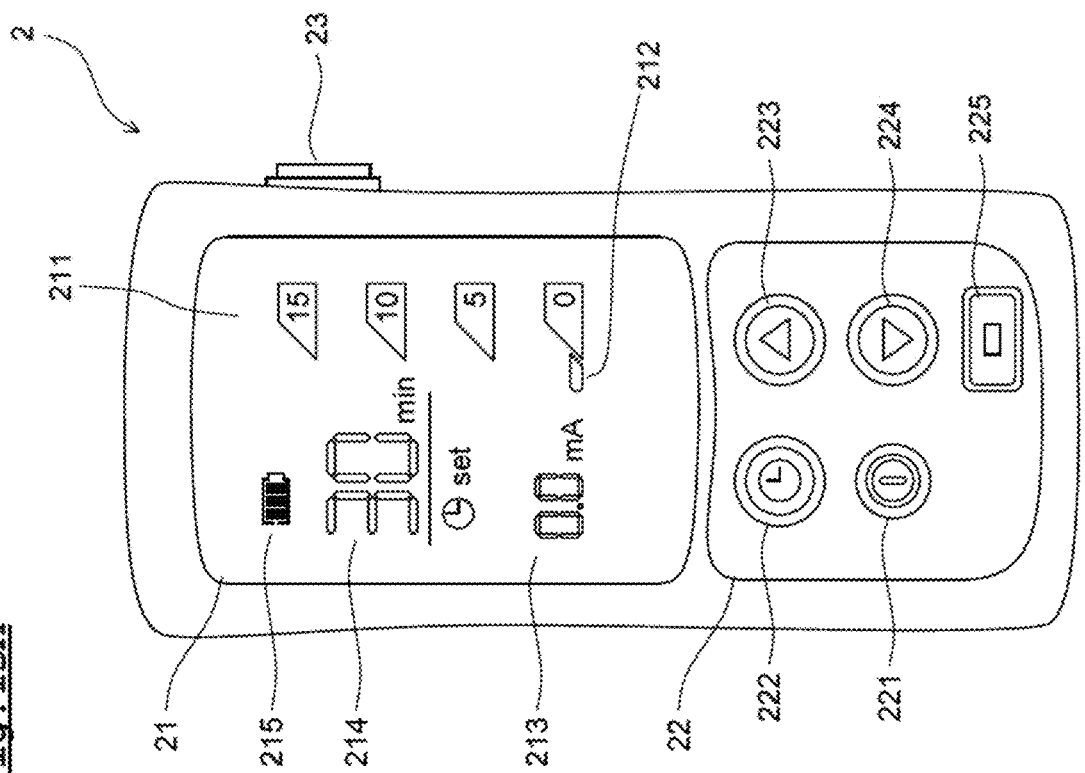

In the process shown in FIG. 9A, the current value Im at the time point when the elapsed time T has reached the threshold time Ts is obtained as the sensory threshold Is. However, as shown in FIG. 13A, a fixation key 225 for fixing the sensory threshold Is may be provided to the operation unit 22, and the current value Im at the time point when the fixation key 225 is operated may be obtained as the sensory threshold Is.

In the process shown in FIG. 9A, obtainment of the sensory threshold Is (S18) and setting and storage of the treatment current value It are performed (S19, S20) in response to the fact that the elapsed time from the timing at which an electrode voltage increasing operation or an electrode voltage decreasing operation had been performed for the first time has reached the time Ts determined in advance. However, obtainment of the sensory threshold Is (S18) and setting and storage of the treatment current value It (S19, S20) may be performed in response to the fact that the elapsed time from the timing at which the electrode voltage increasing operation or the electrode voltage decreasing operation had been performed for the last time has reached the time Ts. In this case, step S13 is deleted from the flow chart shown in FIG. 9A.

In the display form shown in FIG. 9B, the strength of the current (including the sensory threshold Is) that percutaneously flows in the neck of the treated person M1 is indicated by a digit indicative of the effective value of the current. However, the display form of the strength of the current that percutaneously flows in the neck is not limited thereto. For example, as shown in FIG. 13B, the level of the strength of the current (including the sensory threshold Is) that percutaneously flows in the neck of the treated person M1 may be displayed in a level region 217, or alternatively, the level of the strength of the current may be indicated by an indicator, similarly to the voltage value.

Figure 14B:
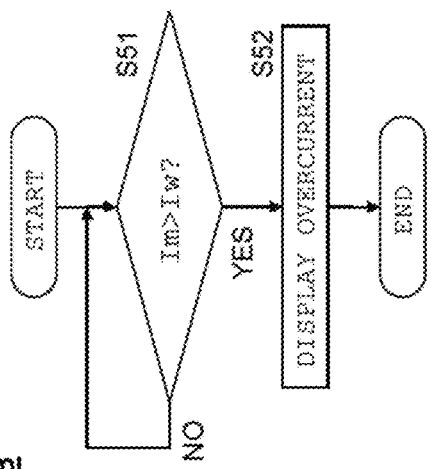
FIGS. 14B and 14C are each a flow chart showing control performed in this modification.
Figure 14C:
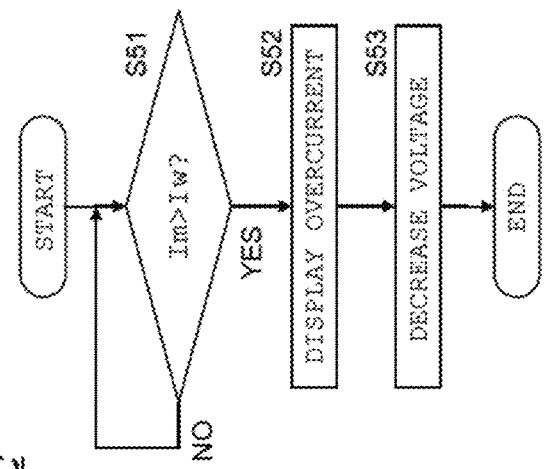
Figure 14A:
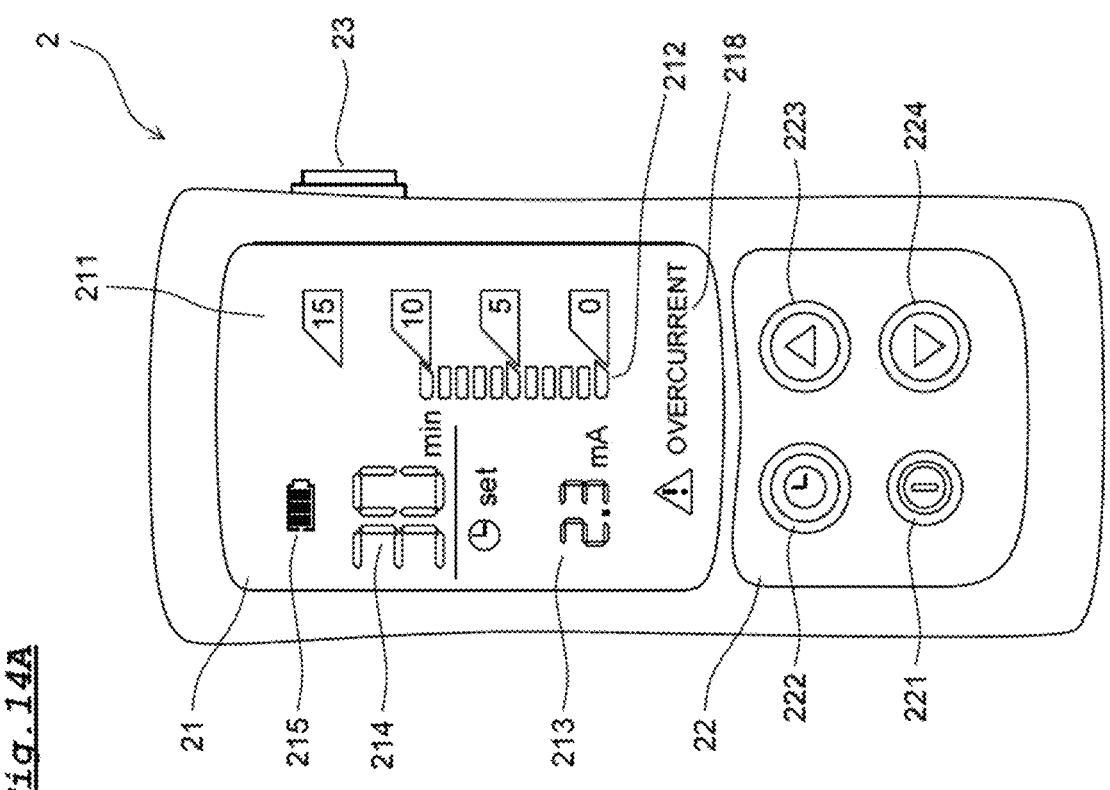
FIG. 14A is a diagram showing a configuration of a screen to be displayed on the display unit of the treatment unit body and a configuration of the operation unit thereof, according to still another modification.

In a case where an excessive current exceeding a predetermined threshold is applied to the neck of the treated person M1 during the process of obtaining the sensory threshold Is or during the treatment process, an alert indication 218 indicative of occurrence of overcurrent may be further displayed as shown in FIG. 14A. In addition, when overcurrent has occurred, a process of automatically lowering the voltage level or of stopping application of voltage may be performed.

In this case, the control unit 27 shown in FIG. 7 performs control shown in FIG. 14B or in FIG. 14C. That is, in the control shown in FIG. 14B, the control unit 27 monitors the current value Im detected by the current detection unit 26 (S51), and when the current value Im has exceeded a threshold Iw (S51: YES), the control unit 27 causes the display unit 21 to display the alert indication 218 shown in FIG. 14A (S52). Alternatively, in the control shown in FIG. 14C, when the current value Im has exceeded the threshold Iw (S51: YES), the control unit 27 additionally lowers the output voltage of the electrodes 33 by a predetermined level (S53). In step S53, the output of voltage by the electrodes 33 may be lowered. Through this control, much discomfort can be suppressed from being given to the treated person M1, and the test and treatment for the treated person M1 can be smoothly carried out. The method of informing occurrence of overcurrent may be another method such as outputting sound or causing a light emitting body to emit light, other than the method of causing the display unit 21 to display the information.

Figure 15B:
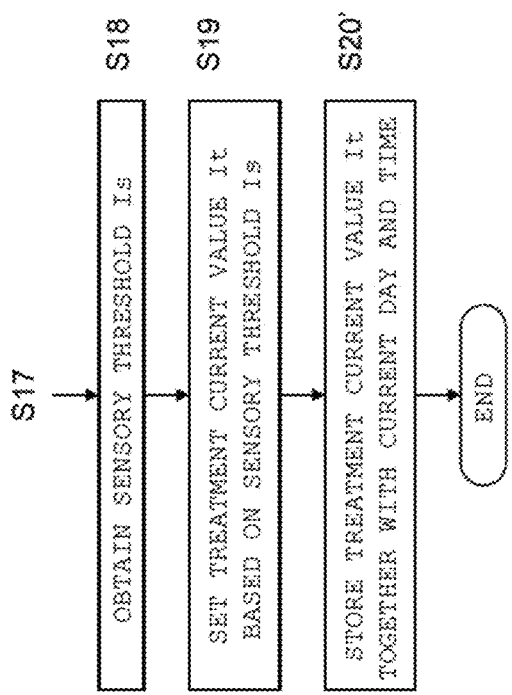
FIG. 15B is a flow chart showing control performed in this modification.
Figure 15A:
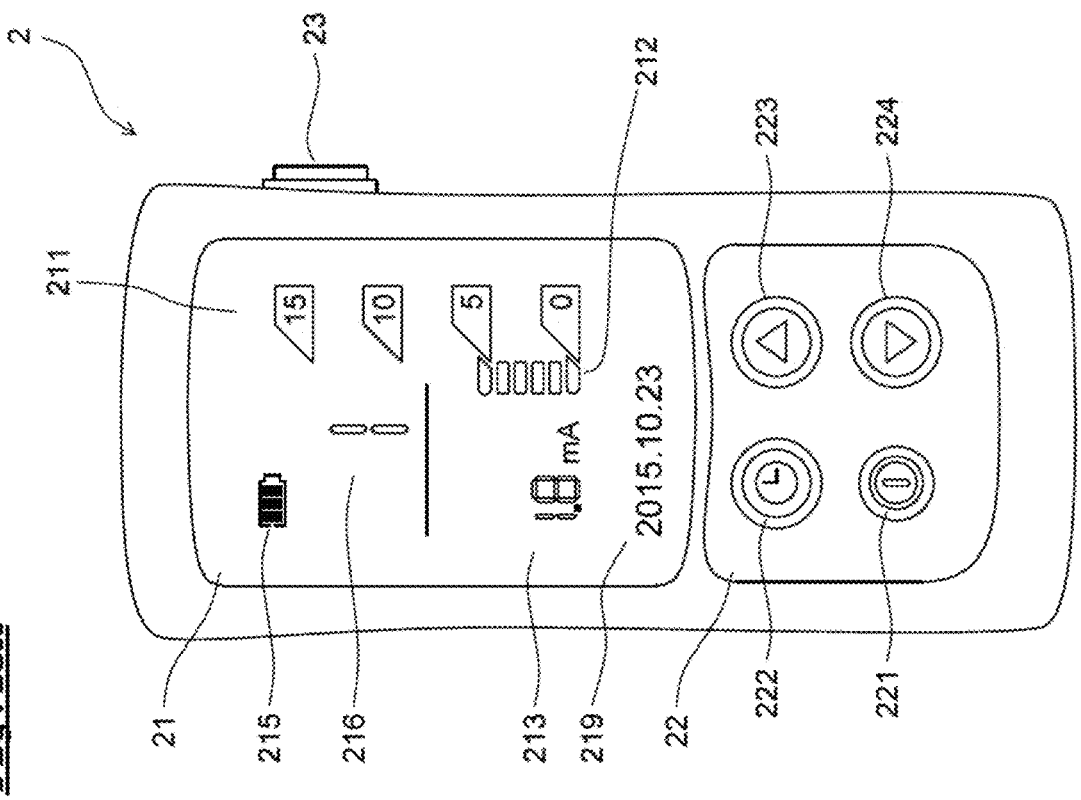
FIG. 15A is a diagram showing a configuration of a screen to be displayed on the display unit of the treatment unit body and a configuration of the operation unit thereof, according to still another modification.

In a case where index information obtained in past treatment is to be displayed, a date 219 on which the index information was obtained may be further displayed as shown in FIG. 15A. In this case, in the storage unit 28, information indicative of the day on which the treatment was performed is stored, together with the index information. In this case, step S20 shown in FIG. 9A is changed to step S20' shown in FIG. 15B, and the treatment current value It is stored in the storage unit 28, together with the current day and time. Thus, the operator can know when the past index information was obtained, and can more properly understand the progress degree of the improvement of dysphagia.

In the example shown in FIGS. 10A to 10C, the voltage and the current applied to the treated person M1 are varied stepwise in accordance with the operation. However, the voltage and the current may not necessarily be varied stepwise, and the voltage and the current may be linearly varied in accordance with operation.

In the configuration example described above, the value of current percutaneously applied to the treated person M1 is adjusted by controlling the voltage. However, the value of current percutaneously applied to the treated person M1 may be adjusted by controlling the current such that the current value measured by the current detection unit 26 is varied in accordance with operation performed on the UP key 223 and the DOWN key 224.

In the process shown in FIG. 9A, in response to the obtainment of the sensory threshold Is, the treatment current value It is automatically set. However, the dysphagia treatment device 1 may be configured such that the operator manually sets the treatment current value It with reference to the displayed sensory threshold Is.

In the configuration shown in FIG. 6A, two pairs the electrodes 33 are attached to the treated person M1. However, the number of pairs of the electrodes 33 attached to the treated person M1 is not limited thereto. As long as an interference wave can be percutaneously applied to the superior laryngeal nerve, etc., the number of pairs of the electrodes 33 attached to the treated person M1 may be one, or three or more. In a case where one pair of the electrodes 33 are used, an interference wave can be caused to percutaneously act on the superior laryngeal nerve, etc. by providing the electrodes 33 with amplitude-modulated current. In this case, the frequency of the amplitude-modulated current has an effect equivalent to that of the beat frequency (treatment frequency).

In the configuration described above, the index information for evaluating the presence or absence and the degree of dysphagia is obtained as a value of current percutaneously applied to the neck of the treated person M1. However, the index information may not be necessarily a current value, and may be another kind of information as long as the information is associated with the sensory threshold.

What is claimed is:
1. A dysphagia test device comprising:
a current application unit configured to be attached to a target portion of a treated person in order to percutaneously apply current to a biological tissue of a neck including superior laryngeal nerve of the treated person;
a processor configured to control the current application unit such that percutaneous stimulation caused by an interference wave or a pseudo interference wave is applied to the biological tissue;
an operation unit configured to adjust the current to be applied by the current application unit, to a sensory threshold at which the treated person becomes aware of the percutaneous stimulation;
a display unit configured to display index information based on the sensory threshold; and
a storage unit in which the index information is stored in chronological order, wherein
the sensory threshold is the smallest value of the current that allows, when the current is percutaneously applied to the neck for several seconds, the treated person to subjectively sense the percutaneous stimulation by the current,
the index information is the sensory threshold or a current value for treatment of dysphagia, the current value being set on the basis of the sensory threshold,
the current application unit includes electrodes which include a positive-side electrode and a negative-side electrode as a pair, the electrodes configured to be adhered to the neck of the treated person,
the processor is configured to determine the sensory threshold by varying voltages to be respectively applied by the electrodes in accordance with an operation performed on the operation unit, thereby to vary the current percutaneously applied to the biological tissue,
the operation unit includes a key for causing the index information stored in the storage unit to be displayed, and
the processor causes the display unit to display the index information stored in the storage unit, in response to an operation performed on the key in order to cause the index information to be displayed.

2. The dysphagia test device according to claim 1, wherein
the current application unit includes two pairs of the electrodes, each pair consisting of a positive-side electrode and a negative-side electrode.

3. The dysphagia test device according to claim 2, wherein
the processor sets a frequency of the current to be applied by each of the two pairs of the electrodes, to a predetermined value in a range of 500 to 8000 Hz, and sets a difference in the frequencies of the currents to be respectively applied by the two pairs of the electrodes, to a predetermined value in a range of 10 to 100 Hz.

4. The dysphagia test device according to claim 1, wherein
the operation unit includes a key for increasing or decreasing the current to be applied by the current application unit, and
the processor increases or decreases the current to be applied by the current application unit, in accordance with an operation performed on the key.

5. The dysphagia test device according to claim 4, wherein the processor stepwise increases or decreases the current to be applied by the current application unit, in accordance with the operation performed on the key.

6. The dysphagia test device according to claim 4, wherein
the processor starts counting time in response to an operation performed on the key, obtains, as the sensory threshold of the treated person, a value of the current being applied by the current application unit at a time point when the counted time has reached a predetermined threshold, and causes the display unit to display the index information on the basis of the obtained current value.

7. The dysphagia test device according to claim 1, wherein
the operation unit includes a key for shifting the index information to be displayed on the display unit, in an order in which the index information has been stored in the storage unit, and
in response to an operation performed on the key for shifting the index information on time base, the processor shifts the index information to be displayed on the display unit, in the order in which the index information has been stored in the storage unit.

8. The dysphagia test device according to claim 1, wherein
when a value of the current being applied by the current application unit has exceeded a predetermined threshold, the processor informs that the value of the current being applied by the current application unit has exceeded the predetermined threshold.

9. A dysphagia treatment device comprising:
a current application unit configured to be attached to a target portion of a treated person in order to percutaneously apply current to a biological tissue of a neck including superior laryngeal nerve of the treated person;
a processor configured to control the current application unit such that percutaneous stimulation caused by an interference wave or a pseudo interference wave is applied to the biological tissue;
an operation unit configured to adjust the current to be applied by the current application unit, to a sensory threshold at which the treated person becomes aware of the percutaneous stimulation;
a display unit configured to display index information based on the sensory threshold and
a storage unit in which the index information is stored in chronological order, wherein
the processor sets a current value for treatment to be provided to the treated person, on the basis of the sensory threshold adjusted through the operation unit,
the sensory threshold is the smallest value of the current that allows, when the current is percutaneously applied to the neck for several seconds, the treated person to subjectively sense the percutaneous stimulation by the current,
the index information is the sensory threshold or a current value for treatment of dysphagia, the current value being set on the basis of the sensory threshold,
the current application unit includes electrodes which include a positive-side electrode and a negative-side electrode as a pair, the electrodes configured to be adhered to the neck of the treated person,
the operation unit includes a key for causing the index information stored in the storage unit to be displayed, and the processor causes the display unit to display the index information stored in the storage unit, in response to an operation performed on the key in order to cause the index information to be displayed.

10. The dysphagia treatment device according to claim 9, wherein
linked with a fact that the sensory threshold has been adjusted through the operation unit, the processor automatically sets for the current application unit the current value for the treatment.

11. The dysphagia treatment device according to claim 10, wherein
as the current value for the treatment, the processor sets the sensory threshold, a current value obtained by raising the sensory threshold by a predetermined level, or a current value obtained by lowering the sensory threshold by a predetermined level.

12. The dysphagia treatment device according to claim 10, wherein
the processor receives a selection of, as the current value for the treatment, the sensory threshold or a current value obtained by varying the sensory threshold by a predetermined level.

13. A dysphagia treatment device comprising:
a current application unit configured to be attached to a target portion of a treated person in order to percutaneously apply current to a biological tissue of a neck including superior laryngeal nerve of the treated person;
a processor configured to control the current application unit such that percutaneous stimulation caused by an interference wave or a pseudo interference wave is applied to the biological tissue;
an operation unit configured to adjust the current to be applied by the current application unit, to a sensory threshold at which the treated person becomes aware of the percutaneous stimulation; and
a storage unit in which the index information is stored in chronological order, wherein
the processor sets, for the current application unit, a current value for treatment to be provided to the treated person, on the basis of the sensory threshold adjusted through the operation unit,
the sensory threshold is the smallest value of the current that allows, when the current is percutaneously applied to the neck for several seconds, the treated person to subjectively sense the percutaneous stimulation by the current,
the current application unit includes electrodes which include a positive-side electrode and a negative-side electrode as a pair, the electrodes configured to be adhered to the neck of the treated person,
the processor is configured to determine the sensory threshold by varying voltages to be respectively applied by the electrodes in accordance with an operation performed on the operation unit, thereby to vary the current percutaneously applied to the biological tissue,
the operation unit includes a key for causing the index information stored in the storage unit to be displayed, and
the processor causes the display unit to display the index information stored in the storage unit, in response to an operation performed on the key in order to cause the index information to be displayed.

* * * * *